United States Patent
Sulaiman et al.

(10) Patent No.: US 11,571,430 B2
(45) Date of Patent: *Feb. 7, 2023

(54) PLATINUM(II) AMMINE SELENOUREA COMPLEXES AND METHODS OF TREATING CANCER

(71) Applicant: KING FAHD UNIVERSITY OF PETROLEUM AND MINERALS, Dhahran (SA)

(72) Inventors: Adam Ahmed Abdullah Sulaiman, Dhahran (SA); Abdul Rajjak Shaikh, Dhahran (SA); Ali Alhoshani, Riyadh (SA); Anvarhusein A. Isab, Dhahran (SA)

(73) Assignees: KING FAHD UNIVERSITY OF PETROLEUM AND MINERALS, Dhahran (SA); KING SAUD UNIVERSITY, Riyadh (SA)

(*) Notice: Subject to any disclaimer, the term of this patent is extended or adjusted under 35 U.S.C. 154(b) by 0 days.

This patent is subject to a terminal disclaimer.

(21) Appl. No.: 17/164,160

(22) Filed: Feb. 1, 2021

(65) Prior Publication Data

US 2021/0283140 A1 Sep. 16, 2021

Related U.S. Application Data

(60) Provisional application No. 62/968,650, filed on Jan. 31, 2020.

(51) Int. Cl.
*A61K 31/555* (2006.01)
*A61K 31/282* (2006.01)

(52) U.S. Cl.
CPC .......... *A61K 31/555* (2013.01); *A61K 31/282* (2013.01)

(58) Field of Classification Search
CPC .............................. A61K 31/555; A61K 31/282
See application file for complete search history.

(56) References Cited

U.S. PATENT DOCUMENTS

| | | | |
|---|---|---|---|
| 4,536,571 A | | 8/1985 | Stockel et al. |
| 4,617,189 A | * | 10/1986 | Stockel ............... C07F 15/0093 424/649 |
| 9,096,505 B2 | | 8/2015 | Robertson et al. |
| 9,974,765 B1 | * | 5/2018 | Jomaa .................. A61K 31/282 |
| 10,358,456 B2 | * | 7/2019 | Isab ..................... A61K 31/555 |
| 10,507,213 B2 | | 12/2019 | Sulaiman et al. |
| 10,533,029 B1 | * | 1/2020 | Isab ........................ A61P 35/00 |
| 2018/0273566 A1 | * | 9/2018 | Isab ........................ A61K 45/06 |
| 2019/0117667 A1 | | 4/2019 | Altoum et al. |

OTHER PUBLICATIONS

Chemistry of Coordination Comopunds, Chapter 24 (online). Pearson Prentice Hall, Inc, 2006. Retrieved from the internet, https://www2.chemistry.msu.edu/courses/cem151/chap24lect_2009.pdf. (Year: 2006).*
Alhoshani et al. Synthesis, X-ray structure and in vitro cytotoxicity of trans-diammineplatinum(II) complexes of selenones, trans-[Pt(NH3)2(selenone)2](NO3)2, Polyhedron, vol. 158, 2019,pp. 234-240, ISSN 0277-5387 (Year: 2019).*
Weers et al. Stereochemistry Blog, "Stereochemistry in Transition Metal Complexes: Metals do Matter," published Oct. 26, 2018. Retrieved from the internet on Jun. 2, 2022, https://blogs.ntu.edu.sg/cy1101-1819s1-g09/2018/10/stereochemistry-in-transition-metal-complexes/ (Year: 2018).*
Adam A.A. Seliman, et al., "Synthesis, X-ray structure, DFT calculations and anticancer activity of a selenourea coordinated gold(I)-carbene complex", POLYHEDRON, vol. 137, Nov. 24, 2017, pp. 197-206 (Abstract only).
Adam A. A. Sulaiman, et al., "Cytotoxic effects of gold(I) complexes against colon, cervical and osteo carcinoma cell lines: a mechanistic approach", New Journal of Chemistry (NJC), vol. 43, Aug. 2019, pp. 14565-14574.
Anja Molter, et al., "Anti-tumour active gold(I), palladium(II) and ruthenium(II) complexes with thio- and selenoureato ligands: a comparative study", Royal Society of Chemistry, Dalton Transactions, vol. 47, Issue 14, Mar. 12, 2018, pp. 5055-5064.

(Continued)

*Primary Examiner* — Brandon J Fetterolf
*Assistant Examiner* — Lauren Wells
(74) *Attorney, Agent, or Firm* — Oblon, McClelland, Maier & Neustadt, L.L.P.

(57) ABSTRACT

A platinum(II) complex of formula (I),

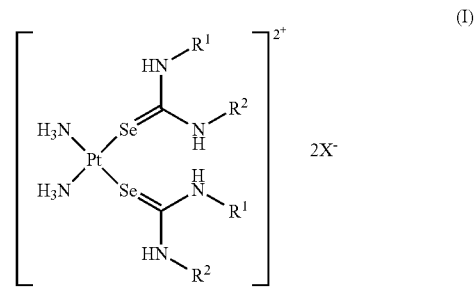

or a pharmaceutically acceptable solvate or tautomer thereof, wherein $R^1$ and $R^2$ are each independently a hydrogen, an optionally substituted alkyl, an optionally substituted cycloalkyl, an optionally substituted arylalkyl, or an optionally substituted aryl; or wherein $R^1$ and $R^2$ together form a five-, six-, or seven-membered ring with the nitrogen atoms to which they are attached; and X is a nitrate anion, a hexafluorophosphate anion, a hexafluoroantimonate anion, a trifluoromethanesulfonate anion, a tetrafluoroborate anion, a perchlorate anion, or a halide anion. A pharmaceutical composition containing the platinum(II) complex of formula (I), and a method of treating cancer are also disclosed.

6 Claims, 21 Drawing Sheets

Specification includes a Sequence Listing.

(56) References Cited

OTHER PUBLICATIONS

Jean-Pierre Girault, et al., "Interaction of cis-[Pt(NH$_3$)$_2$(H$_2$O)$_2$](NO$_3$)$_2$ with Ribose and Deoxyribose Diguanosine Phosphates", Biochemistry, vol. 21, No. 6, Mar. 16, 1982, pp. 1352-1356.

\* cited by examiner

1) Selenourea (Seu) (1)
2) N,N'-dimethylselenourea (Me2Seu) (2)
3) 1,3-Imidazolidine-2-selenone (ImSe) (3)
4) 1,3-Diazinane-2-selenone (DiazSe) (4)
5) 1,3-Diazepane-2-selenone (DiapSe) (5)

L = Selenone ligand

PLATINUM(II) AMMINE SELENOUREA COMPLEXES AND METHODS OF TREATING CANCER

CROSS REFERENCE TO RELATED APPLICATIONS

This application claims the benefit of U.S. Provisional Application No. 62/968,650 filed Jan. 31, 2020, which is incorporated herein by reference in its entirety.

REFERENCE TO A SEQUENCE LISTING

In accordance with 37 CFR § 1.52(e)(5), the present specification makes reference to a Sequence Listing submitted electronically as a .txt file named 528347US_ST25.txt". The .txt file was generated on Mar. 20, 2020 and is 0.607 kb in size. The entire contents of the Sequence Listing are herein incorporated by reference.

STATEMENT OF ACKNOWLEDGEMENT

The financial support of this work by King Fahd University of Petroleum & Minerals (KFUPM) under Project No. IN171005 is gratefully acknowledged.

BACKGROUND OF THE INVENTION

Technical Field

The present disclosure relates to platinum(II) ammine selenourea complexes with anticancer or antitumor properties, and pharmaceutical compositions and uses thereof.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Cisplatin, cis-diamminedichloridoplatinum(II), is one of the most successful drugs used in the clinics for the treatment of testicular, bladder, lung and ovarian cancers. See Kelland L (2007), The resurgence of platinum-based cancer chemotherapy. Nat Rev Cancer 7:573-584; Lovejoy K S, Lippard S J (2009) Non-traditional platinum compounds for improved accumulation, oral bioavailability, and tumor targeting. Dalt Trans 0:10651; Wheate N J, Walker S, Craig G E, Oun R (2010), The status of platinum anticancer drugs in the clinic and in clinical trials. Dalt Trans 39:8113; Dasari S, Bernard Tchounwou P (2014) Cisplatin in cancer therapy: Molecular mechanisms of action. Eur J Pharmacol 740:364-378; Wilson J J, Lippard S J (2014) Synthetic methods for the preparation of platinum anticancer complexes. Chem Rev 114:4470-95; Gay M, Montaña Á M, Batalla C, et al (2015) Design, synthesis and SAR studies of novel 1,2-bis (aminomethyl)cyclohexane platinum(II) complexes with cytotoxic activity. Studies of interaction with DNA of iodinated seven-membered 1,4-diaminoplatinocycles. J Inorg Biochem 142:15-27; Dilruba S, Kalayda G V (2016) Platinum-based drugs: Past, present and future. Cancer Chemother Pharmacol 77:1103-1124; Fennell D A, Summers Y, Cadranel J, et al (2016) Cisplatin in the modern era: The backbone of first-line chemotherapy for non-small cell lung cancer. Cancer Treat Rev 44:42-50; Johnstone T C, Suntharalingam K, Lippard S J (2016) The Next Generation of Platinum Drugs: Targeted Pt(II) Agents, Nanoparticle Delivery, and Pt(IV) Prodrugs. Chem Rev 116:3436-86; Ho G Y, Woodward N, Coward J I G (2016) Cisplatin versus carboplatin: comparative review of therapeutic management in solid malignancies. Crit Rev Oncol Hematol 102:37-46; Ahmad S (2017) Kinetic aspects of platinum anticancer agents. Polyhedron 138:109-124; Savić A, Marzo T, Scaletti F, et al (2019) New platinum(II) and palladium(II) complexes with substituted terpyridine ligands: synthesis and characterization, cytotoxicity and reactivity towards biomolecules. BioMetals 32:33-47; and de Camargo M S, De Grandis R A, da Silva M M, et al (2019) Determination of in vitro absorption in Caco-2 monolayers of anticancer Ru(II)-based complexes acting as dual human topoisomerase and PARP inhibitors. BioMetals 32:89-100, each incorporated herein by reference in their entirety.

Despite the remarkable success of cisplatin in the treatment of testicular and ovarian cancers, two major limitations of the drug have limited its widespread use in high doses. These are; (i) its toxic side effects, especially nephrotoxicity, neurotoxicity, ototoxicity and gastrointestinal toxicity, and (ii) its inactivity against some of the most frequent human tumor types (e.g., colon and non-small cell lung cancers) due to the emergence of drug resistance. See Hartmann J T, Lipp H-P (2003) Toxicity of platinum compounds. Expert Opin Pharmacother 4:889-901; Florea A-M, Büsselberg D (2011) Cisplatin as an Anti-Tumor Drug: Cellular Mechanisms of Activity, Drug Resistance and Induced Side Effects. Cancers (Basel) 3:1351-1371; Piccolini V M, Bottone M G, Bottiroli G, et al (2013) Platinum drugs and neurotoxicity: Effects on intracellular calcium homeostasis. Cell Biol Toxicol 29:339-353; Dasari S, Bernard Tchounwou P (2014) Cisplatin in cancer therapy: Molecular mechanisms of action. Eur J Pharmacol 740:364-378; Zisowsky J, Koegel S, Leyers S, et al (2007) Relevance of drug uptake and efflux for cisplatin sensitivity of tumor cells. Biochem Pharmacol 73:298-307; Stewart D J (2007) Mechanisms of resistance to cisplatin and carboplatin. Crit Rev Oncol Hematol 63:12-31; Florea A-M, Büsselberg D (2011) Cisplatin as an Anti-Tumor Drug: Cellular Mechanisms of Activity, Drug Resistance and Induced Side Effects. Cancers (Basel) 3:1351-1371; Senovilla L, Galluzzi L, Marino G, et al (2012) Immunosurveillance against cancer-associated hyperploidy. Oncotarget 3, 1270-1271; and Shen D-W, Pouliot L M, Hall M D, Gottesman M M (2012) Cisplatin resistance: a cellular self-defense mechanism resulting from multiple epigenetic and genetic changes. Pharmacol Rev 64:706-21, each incorporated herein by reference in their entirety. These limitations stressed the necessity for the search of new platinum complexes endowed with less side effects and capable of overcoming the resistance to cisplatin. See Lebwohl D, Canetta R (1998) Clinical development of platinum complexes in cancer therapy: An historical perspective and an update. Eur J Cancer 34:1522-1534; Kelland L R, Sharp S Y, O'Neill C F, et al (1999) Mini-review: Discovery and development of platinum complexes designed to circumvent cisplatin resistance. J Inorg Biochem 77:111-115; Galanski M, Jakupec M, Keppler B (2005) Update of the Preclinical Situation of Anticancer Platinum Complexes: Novel Design Strategies and Innovative Analytical Approaches. Curr Med Chem 12:2075-2094; Reedijk J (2009) Platinum Anticancer Coordination Compounds: Study of DNA Binding Inspires New Drug Design. Eur J Inorg Chem 2009:1303-1312; Wheate N J, Walker S, Craig G E, Oun R (2010) The status of platinum anticancer drugs in the clinic and in clinical trials. Dalt Trans 39:8113; Wilson J J, Lippard S J (2014) Synthetic methods for the preparation of platinum anticancer complexes. Chem Rev 114:4470-95; Dilruba S, Kalayda G V (2016) Platinum-based drugs: Past, present and future. Cancer Chemother Pharmacol 77:1103-1124; Bai L, Gao C, Liu Q, et al (2017) Research progress in modern structure of platinum complexes. Eur J Med Chem 140:349-382; and Štarha P, Vančo J, Trávníček Z (2017) Platinum complexes containing adenine-based ligands: An overview of selected structural features. Coord Chem Rev 332:1-29, each incorporated herein by reference in their entirety. Consequently, several derivatives of cisplatin, carboplatin and oxaliplatin have been prepared and tested for their antitumor activity. See Kelland L R, Sharp S Y, O'Neill C F, et al (1999) Mini-review: Discovery and development of platinum complexes designed to circumvent cisplatin resistance. J Inorg Biochem 77:111-115; Bernhardt G, Brunner H, Gruber N, et al (2004) Carboplatin derivatives with superior antitumor activity compared to the parent compound. Inorganica Chim Acta 357:4452-4466; Carland M, Abrahams B F, Rede T, et al (2006) Syntheses and structural studies of platinum(II) complexes of O-methylselenomethionine and related ligands. Inorganica Chim Acta 359:3252-3256; Kostova I (2006) Platinum Complexes as Anticancer Agents. Recent Pat Anticancer Drug Discov 1:1-22; Marverti G, Cusumano M, Ligabue A, et al (2008) Studies on the anti-proliferative effects of novel DNA-intercalating bipyridyl-thiourea-Pt(II) complexes against cisplatin-sensitive and -resistant human ovarian cancer cells. J Inorg Biochem 102:699-712; Kovala-Demertzi D, Papageorgiou A, Papathanasis L, et al (2009) In vitro and in vivo antitumor activity of platinum(II) complexes with thiosemicarbazones derived from 2-formyl and 2-acetyl pyridine and containing ring incorporated at N(4)-position: Synthesis, spectroscopic study and crystal structure of platinum(II) c. Eur J Med Chem 44:1296-1302; Starha P, Trávnícek Z, Popa I (2010) Platinum(II) oxalato complexes with adenine-based carrier ligands showing significant in vitro antitumor activity. J Inorg Biochem 104:639-647; Fuks L, Anuszewska E, Kruszewska H, et al (2010) Platinum(II) complexes with thiourea derivatives containing oxygen, sulfur or selenium in a heterocyclic ring: Computational studies and cytotoxic properties. Transit Met Chem 35:639-647; Tamasi G, Casolaro M, Magnani A, et al (2010) New platinum-oxicam complexes as anti-cancer drugs. Synthesis, characterization, release studies from smart hydrogels, evaluation of reactivity with selected proteins and cytotoxic activity in vitro. J Inorg Biochem 104:799-814; Yin R, Gou S, Liu X, Lou L (2011) Antitumor activities and interaction with DNA of oxaliplatin-type platinum complexes with linear or branched alkoxyacetates as leaving groups. J Inorg Biochem 105:1095-1101; Escribano E, Font-Bardia M, Calvet T, et al (2013) DNA binding studies of a series of cis-[Pt(Am)2X2] complexes (Am=inert amine, X=labile carboxylato ligand). Inorganica Chim Acta 394:65-76; Zeng L, Li Y, Li T, et al (2014) Selenium-platinum coordination compounds as novel anticancer drugs: Selectively killing cancer cells via a reactive oxygen species (ROS)-mediated apoptosis route. Chem Asian J 9:2295-2302; Pracharova J, Saltarella T, Radosova Muchova T, et al (2015) Novel antitumor cisplatin and transplatin derivatives containing 1-methyl-7-azaindole: Synthesis, characterization, and cellular responses. J Med Chem 58:847-859; Gay M, Montaña ÁM, Batalla C, et al (2015) Design, synthesis and SAR studies of novel 1,2-bis(aminomethyl)cyclohexane platinum (II) complexes with cytotoxic activity. Studies of interaction with DNA of iodinated seven-membered 1,4-diaminoplatinocycles. J Inorg Biochem 142:15-27; Chopade S M, Phadnis P P, Hodage A S, et al (2015) Synthesis, characterization, structures and cytotoxicity of platinum(II) complexes containing dimethylpyrazole based selenium ligands. Inorganica Chim Acta 427:72-80; Křikavová R, Vančo J, Šilha T, et al (2016) Synthesis, characterization, DNA binding studies and in vitro cytotoxicity of platinum(II)-dihalogenido complexes containing bidentate chelating N-donor ligands. J Coord Chem 69:2422-2436; Miles B A, Patterson A E, Vogels C M, et al (2016) Synthesis, characterization, and anticancer activities of lipophilic pyridinecarboxaldimine platinum(II) complexes. Polyhedron 108:23-29; Bai L, Gao C, Liu Q, et al (2017) Research progress in modern structure of platinum complexes. Eur J Med Chem 140:349-382; Starha P, Vančo J, Trávníček Z (2017) Platinum complexes containing adenine-based ligands: An overview of selected structural features. Coord Chem Rev 332: 1-29; Intini F P, Zajac J, Novohradsky V, et al (2017) Novel Antitumor Platinum(II) Conjugates Containing the Nonsteroidal Anti-inflammatory Agent Diclofenac: Synthesis and Dual Mechanisms of Antiproliferative Effects. Inorg Chem 56:1483-1497; and Jomaa M Y, Ahmad S, Seliman A A A, et al (2019) Synthesis, spectroscopic characterization and in vitro cytotoxic as well as docking studies of cis-diammine platinum(II) complexes of thiones. Inorganica Chim Acta 484:347-351, each incorporated herein by reference in their entirety. A few cisplatin derivatives contain selenoether ligands, such as selenomethionine. See Kelland L R, Sharp S Y, O'Neill C F, et al (1999) Mini-review: Discovery and development of platinum complexes designed to circumvent cisplatin resistance. J. Inorg Biochem 77:111-115; Bernhardt G, Brunner H, Gruber N, et al (2004) Carboplatin derivatives with superior antitumor activity compared to the parent compound. Inorganica Chim Acta 357:4452-4466; Carland M, Abrahams B F, Rede T, et al (2006) Syntheses and structural studies of platinum(II) complexes of O-methylselenomethionine and related ligands. Inorganica Chim Acta 359:3252-3256; Kostova I (2006) Platinum Complexes as Anticancer Agents. Recent Pat Anticancer Drug Discov 1:1-22; Marverti G, Cusumano M, Ligabue A, et al (2008) Studies on the anti-proliferative effects of novel DNA-intercalating bipyridyl-thiourea-Pt(II) complexes against cisplatin-sensitive and -resistant human ovarian cancer cells. J Inorg Biochem 102:699-712; Kovala-Demertzi D, Papageorgiou A, Papathanasis L, et al (2009) In vitro and in vivo antitumor activity of platinum(II) complexes with thiosemicarbazones derived from 2-formyl and 2-acetyl pyridine and containing ring incorporated at N(4)-position: Synthesis, spectroscopic study and crystal structure of platinum(II) c. Eur J Med Chem 44:1296-1302; Starha P, Trávnícek Z, Popa I (2010) Platinum(II) oxalato complexes with adenine-based carrier ligands showing significant in vitro antitumor activity. J Inorg Biochem 104:639-647; Fuks L, Anuszewska E, Kruszewska H, et al (2010) Platinum(II) complexes with thiourea derivatives containing oxygen, sulfur or selenium in a heterocyclic ring: Computational studies and cytotoxic properties. Transit Met Chem 35:639-647; Tamasi G, Casolaro M, Magnani A, et al (2010) New platinum-oxicam complexes as anti-cancer drugs. Synthesis, characterization, release studies from smart hydrogels, evaluation of reactivity with selected proteins and cytotoxic activity in vitro. J Inorg Biochem 104:799-814; Yin R, Gou S, Liu X, Lou L (2011) Antitumor activities and interaction with DNA of oxaliplatin-type platinum complexes with linear or branched alkoxyacetates as leaving groups. J Inorg Biochem 105:1095-1101; Escribano E, Font-Bardia M, Calvet T, et al (2013) DNA binding studies of a series of cis-[Pt(Am)$_2$X$_2$] complexes (Am=inert amine, X=labile carboxylato ligand). Inorganica Chim Acta 394:65-76; Zeng L, Li Y, Li T, et al (2014) Selenium-platinum coordination compounds as novel anticancer drugs: Selectively killing cancer cells via a reactive oxygen species (ROS)-mediated apoptosis route. Chem Asian J 9:2295-2302; Pracharova J, Saltarella T, Radosova Muchova T, et al (2015) Novel antitumor cisplatin and transplatin derivatives containing 1-methyl-7-azaindole: Synthesis, characterization, and cellular responses. J Med Chem 58:847-859; Gay M, Montaña ÁM, Batalla C, et al (2015) Design, synthesis and SAR studies of novel 1,2-bis(aminomethyl)cyclohexane platinum (II) complexes with cytotoxic activity. Studies of interaction with DNA of iodinated seven-membered 1,4-diaminoplatinocycles. J Inorg Biochem 142:15-27; Chopade S M, Phadnis P P, Hodage A S, et al (2015) Synthesis, characterization, structures and cytotoxicity of platinum(II) complexes containing dimethylpyrazole based selenium ligands. Inorganica Chim Acta 427:72-80; Křikavová R, Vančo J, Šilha T, et al (2016) Synthesis, characterization, DNA binding studies and in vitro cytotoxicity of platinum(II)-dihalogenido complexes containing bidentate chelating N-donor ligands. J Coord Chem 69:2422-2436; Miles B A, Patterson A E, Vogels C M, et al (2016) Synthesis, characterization, and anticancer activities of lipophilic pyridinecarboxaldimine platinum(II) complexes. Polyhedron 108:23-29; Bai L, Gao C, Liu Q, et al (2017) Research progress in modern structure of platinum complexes. Eur J Med Chem 140:349-382; Štarha P, Vančo J, Trávníček Z (2017) Platinum complexes containing adenine-based ligands: An overview of selected structural features. Coord Chem Rev 332: 1-29; Intini F P, Zajac J, Novohradsky V, et al (2017) Novel Antitumor Platinum(II) Conjugates Containing the Nonsteroidal Anti-inflammatory Agent Diclofenac: Synthesis and Dual Mechanisms of Antiproliferative Effects. Inorg Chem 56:1483-1497; and Jomaa M Y, Ahmad S, Seliman A A A, et al (2019) Synthesis, spectroscopic characterization and in vitro cytotoxic as well as docking studies of cis-diammine platinum(II) complexes of thiones. Inorganica Chim Acta 484:347-351, each incorporated herein by reference in their entirety. The selenium containing compounds have been exploited in an effort to reduce the toxicity of platinum drugs, because selenomethionine has been shown to reduce the renal toxicity of cisplatin in rats and mice. See Sreejayan, Rao M N (1997) Nitric oxide scavenging by curcuminoids. J Pharm Pharmacol 49:105-7, incorporated herein by reference in its entirety. In this regard, the inventors have recently reported the synthesis, characterization and antitumor properties of a variety of platinum(II) complexes of selenones, which include; [Pt(Selenone)$_2$Cl$_2$], [Pt(Selenone)$_4$]Cl$_2$ transplatin derivatives, trans-[Pt(NH$_3$)$_2$(Selenone)$_2$](NO$_3$)$_2$. See Altoum A O S, Alhoshani A, Alhosaini K, et al (2017a) Synthesis, characterization and in vitro cytotoxicity of platinum(II) complexes of selenones [Pt(selenone) 2 Cl 2]. J Coord Chem 70:1020-1031; Altoum A O S, Vančo J, Křikavová R, et al (2017b) Synthesis, structural characterization and cytotoxicity evaluation of platinum(II) complexes of heterocyclic selenones. Polyhedron 128: 2-8; Ahmad S, Altoum A O S, Vančo J, et al (2018) Synthesis, crystal structure and anticancer activity of tetrakis (N-isopropylimidazolidine-2-selenone)platinum(II) chloride. J Mol Struct 1152:232-236; and Alhoshani A, Seliman A A A, Altoum A O, et al (2019) Synthesis, X-ray structure and in vitro cytotoxicity of trans-diammineplatinum(II) complexes of selenones, trans-[Pt(NH$_3$)$_2$(selenone)$_2$] (NO$_3$)$_2$. Polyhedron 158:234-240, each incorporated herein by reference in their entirety.

In view of the forgoing, one objective of the present disclosure is to provide safe and potent therapeutic complexes with low- and sub-micromolar antiproliferative activity based on cis-platinum(II) ammine complexes containing selenourea ligands, a pharmaceutical composition containing the platinum(II) complexes, and a method for treating cancer with the platinum(II) complexes.

BRIEF SUMMARY OF THE INVENTION

Accordingly, it is one object of the present invention to provide a platinum(II) complex of formula (T),

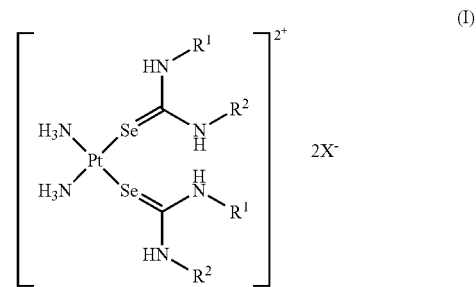

(I)

or a pharmaceutically acceptable solvate or tautomer thereof, wherein:

$R^1$ and $R^2$ are each independently a hydrogen, an optionally substituted alkyl, an optionally substituted cycloalkyl, an optionally substituted arylalkyl, or an optionally substituted aryl; or wherein $R^1$ and $R^2$ together form a five-, six-, or seven-membered ring with the nitrogen atoms to which they are attached; and X is a nitrate anion, a hexafluorophosphate anion, a hexafluoroantimonate anion, a trifluoromethanesulfonate anion, a tetrafluoroborate anion, a perchlorate anion, or a halide anion.

In some embodiments, $R^1$ and $R^2$ are the same.

In some embodiments, $R^1$ and $R^2$ are each independently hydrogen or an optionally substituted alkyl.

In some embodiments, $R^1$ and $R^2$ are each independently hydrogen or an optionally substituted $C_1$ to $C_5$ alkyl.

In some embodiments, $R^1$ and $R^2$ are each hydrogen.

In some embodiments, $R^1$ and $R^2$ are each methyl.

In some embodiments, $R^1$ and $R^2$ together form a five-, six-, or seven-membered ring with the nitrogen atoms to which they are attached.

In some embodiments, $R^1$ and $R^2$ together form a five- or six-membered ring with the nitrogen atoms to which they are attached.

In some embodiments, R¹ and R² together form a five-membered ring with the nitrogen atoms to which they are attached.

In some embodiments, X is a nitrate anion.

In some embodiments, the platinum(II) complex of formula (I) is selected from the group consisting of

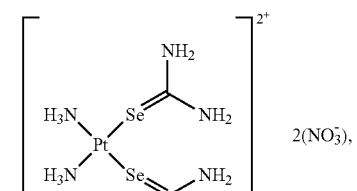

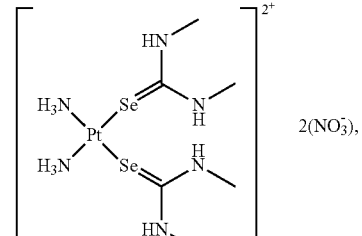

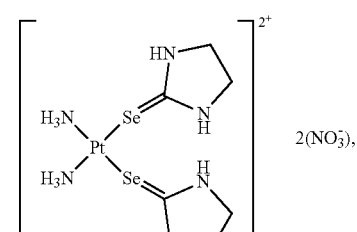

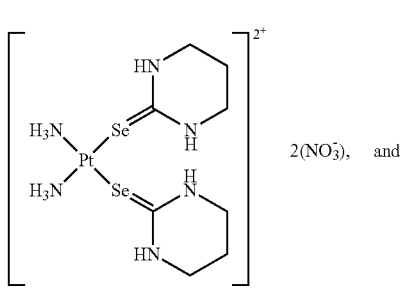

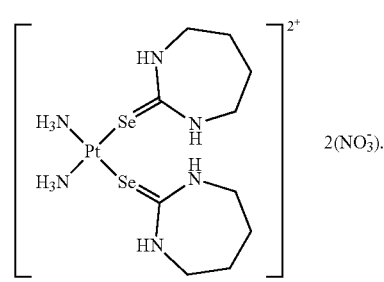

In some embodiments, the platinum(II) complex of formula (I) is

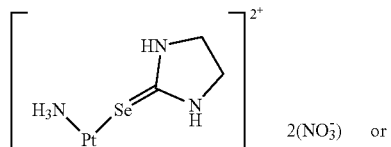

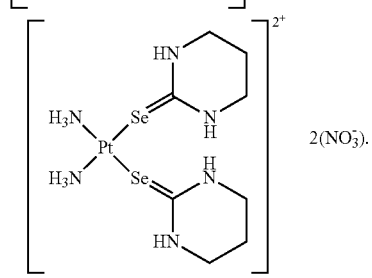

It is another object of the present invention to provide a pharmaceutical composition containing the platinum(II) complex of formula (I), and a pharmaceutically acceptable carrier and/or excipient.

In some embodiments, the platinum(II) complex of formula (I) is present in the pharmaceutical composition in a concentration of 0.1 to 100 μM, relative to a total volume of the pharmaceutical composition.

In some embodiments, the pharmaceutically acceptable carrier and/or excipient comprises dimethyl sulfoxide.

It is yet another object of the present invention to provide a method for treating cancer in a subject, involving administering to the subject a therapeutically effective amount of the platinum(II) complex of formula (I), wherein the cancer is at least one selected from the group consisting of cervical cancer, lung cancer, and colon cancer.

In some embodiments, the therapeutically effective amount of the platinum(II) complex of formula (I) is from 0.01 to 100 mg/kg of the platinum(II) complex of formula (I) per body weight of the subject.

In some embodiments, the cancer is resistant to at least one platinum-based chemotherapy drug having at least one chloro ligand.

In some embodiments, the platinum-based chemotherapy drug having at least one chloro ligand is cisplatin.

In some embodiments, the subject is a human.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 7A illustrates Complex 5 in the minor groove of 1BNA, FIG. 1B is a surface representation of the binding interaction of FIG. 7A, and FIG. 7C shows the hydrogen bond interactions of complex 5 with residues DC-9 and DG-10;

DETAILED DESCRIPTION OF THE EMBODIMENTS

Figure 1A:
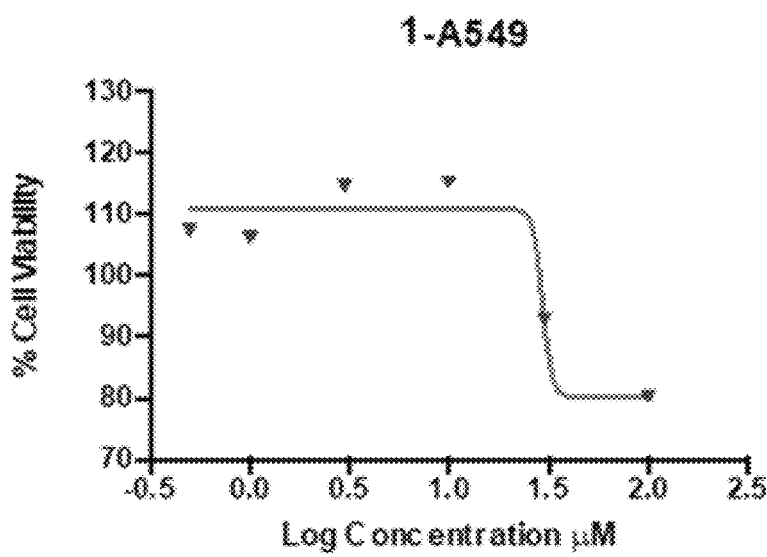
FIGS. 1A-1F are graphs illustrating the effect of concentration of cis-[Pt(NH$_3$)$_2$(selenone)$_2$](NO$_3$)$_2$ complexes 1 (FIG. 1A), 2 (FIG. 1B), 3 (FIG. 1C), 4 (FIG. 1D), 5 (FIG. 1E), and cisplatin ("Cis") (FIG. 1F) on the percentage viability of A549 (lung cancer cells)
Figure 1B:
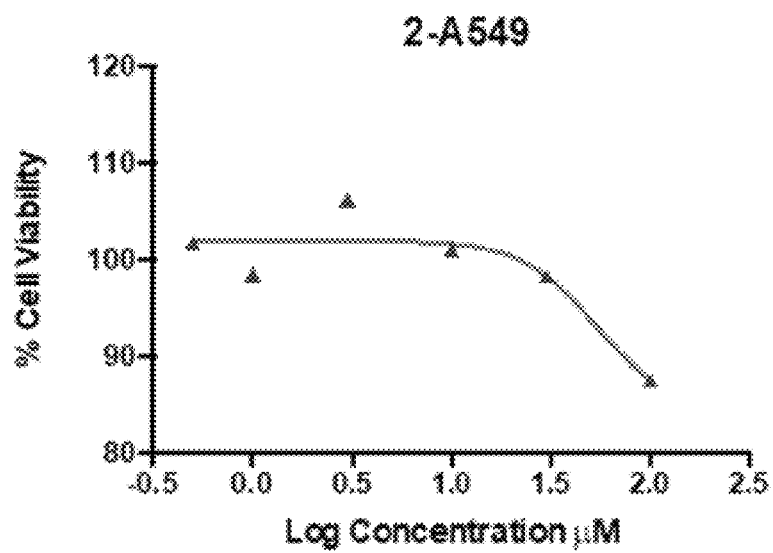
Figure 1C:
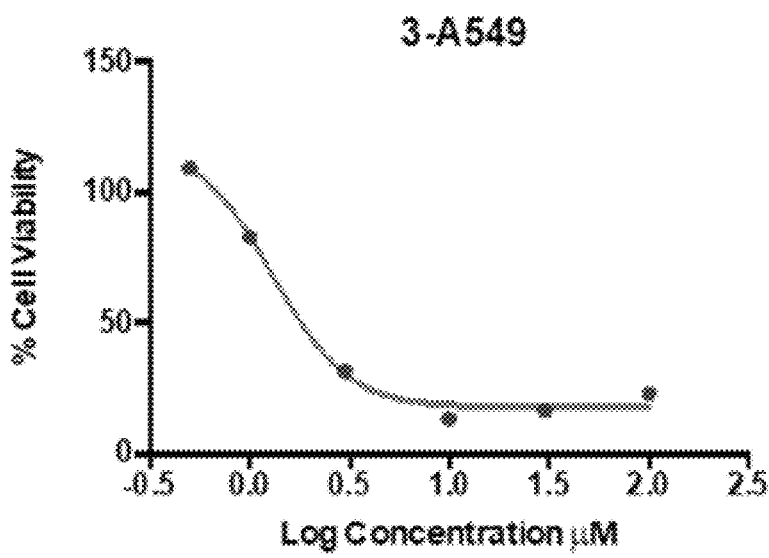
Figure 1D:
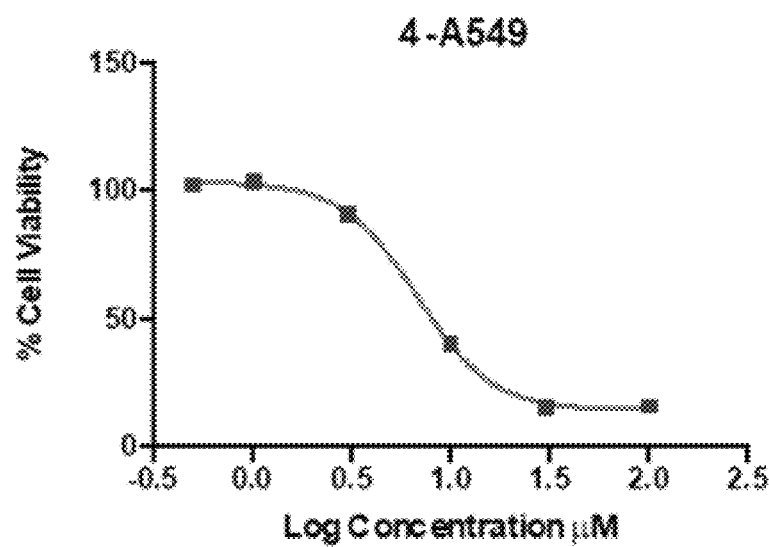
Figure 1E:
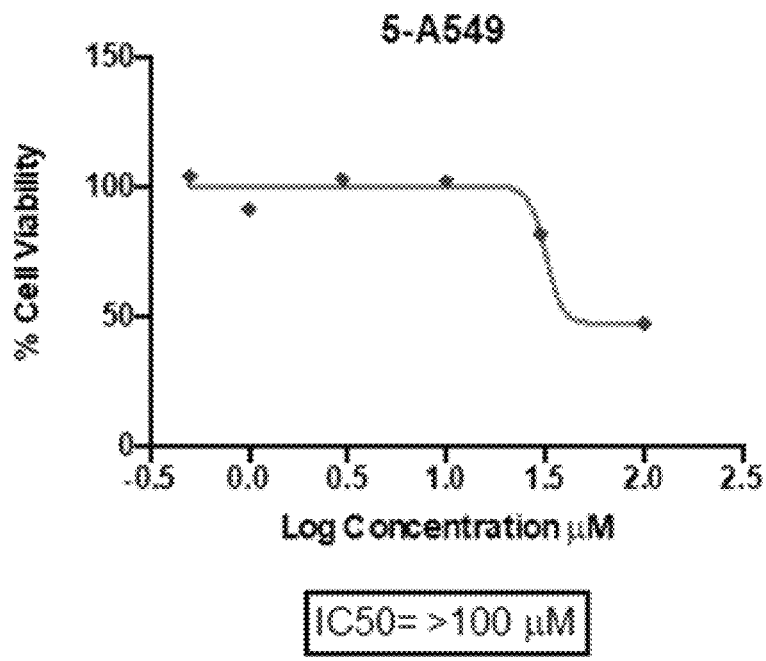
Figure 1F:
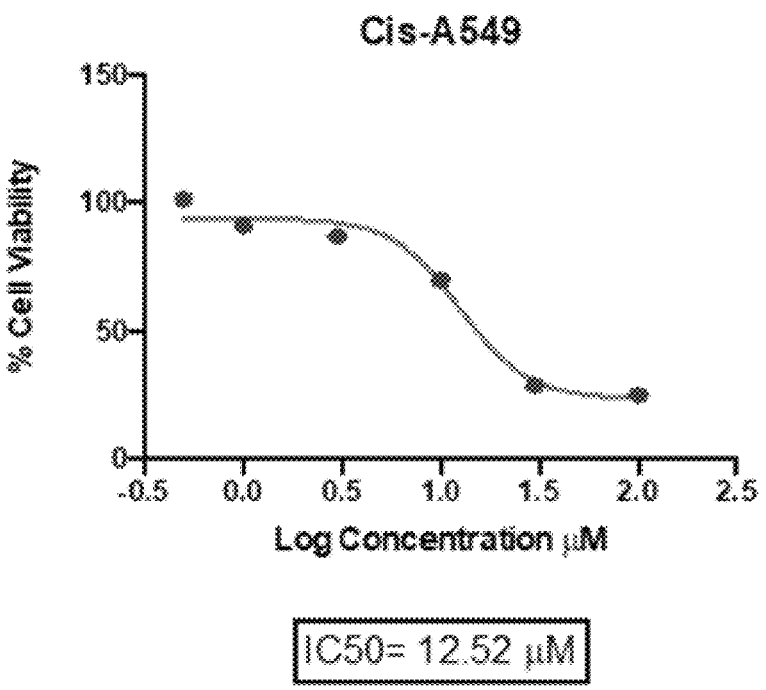
Figure 2:
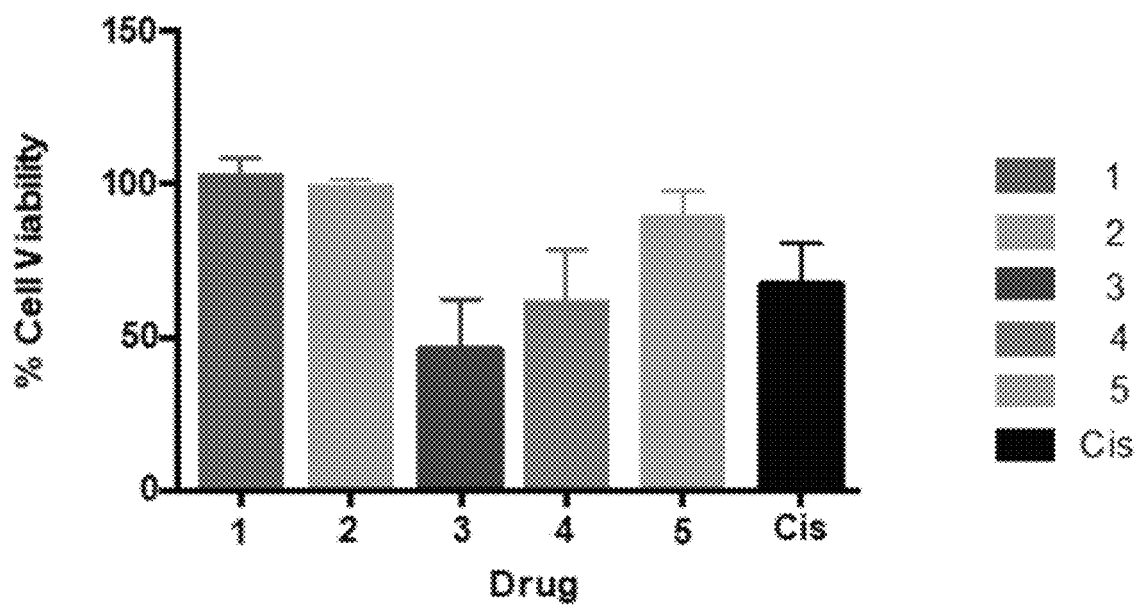
FIG. 2 is a bar graph illustrating the effect of cis-[Pt(NH$_3$)$_2$(selenone)$_2$](NO$_3$)$_2$ complexes (1-5) and cisplatin on the percentage viability of A549 (lung cancer cells)
Figure 3A:
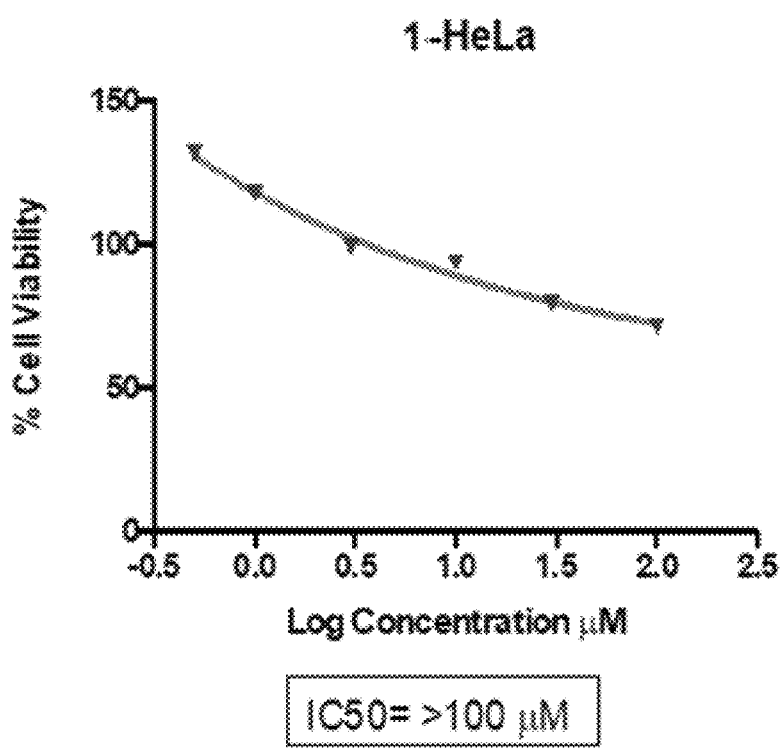
FIGS. 3A-3F are graphs illustrating the effect of concentration of cis-[Pt(NH$_3$)$_2$(selenone)$_2$](NO$_3$)$_2$ complexes 1 (FIG. 3A), 2 (FIG. 3B), 3 (FIG. 3C), 4 (FIG. 3D), 5 (FIG. 3E), and cisplatin ("Cis") (FIG. 3F) on the percentage viability of HeLa (cervical cancer cells)
Figure 3B:
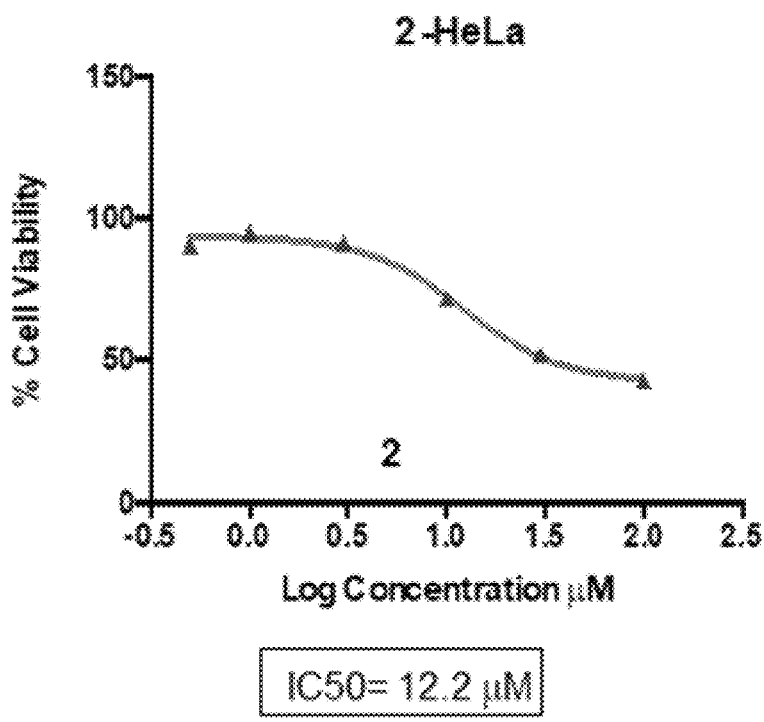
Figure 3C:
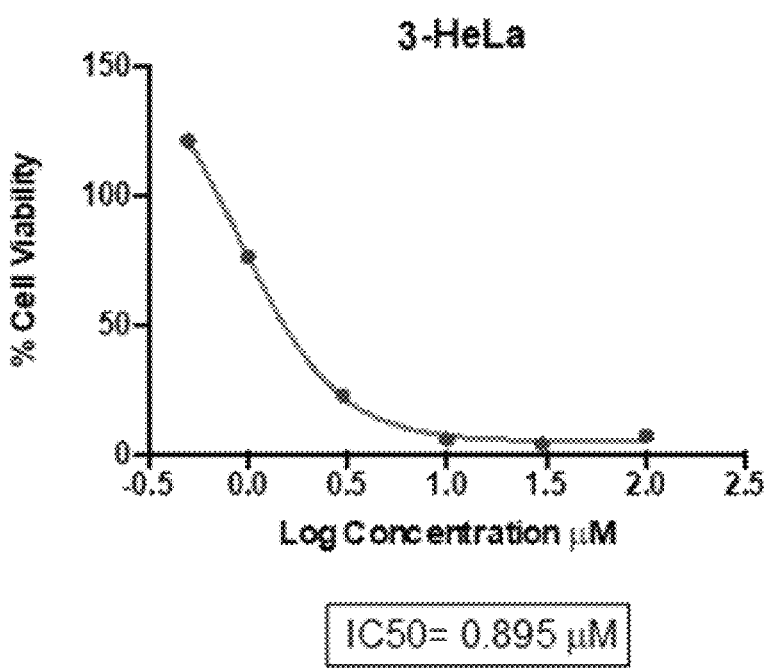
Figure 3D:
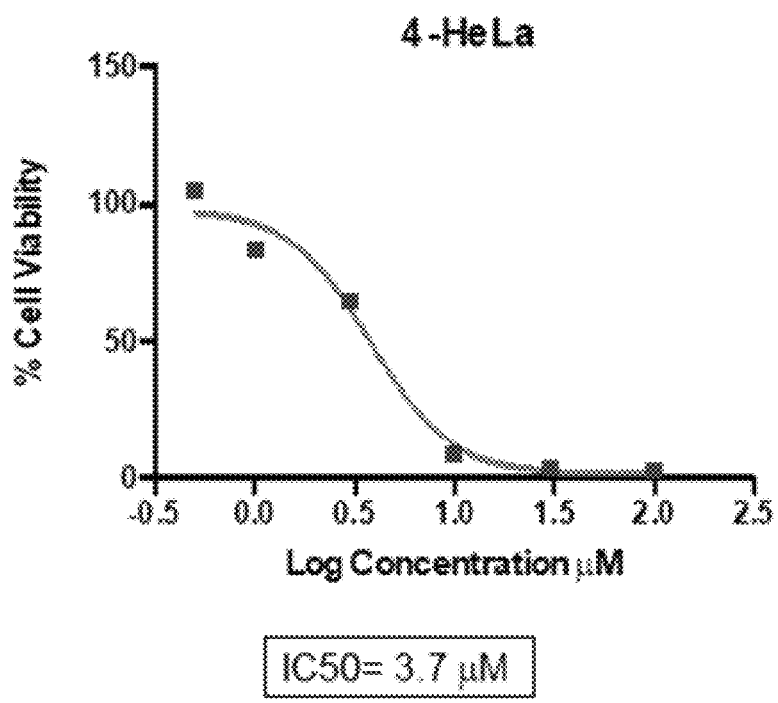
Figure 3E:
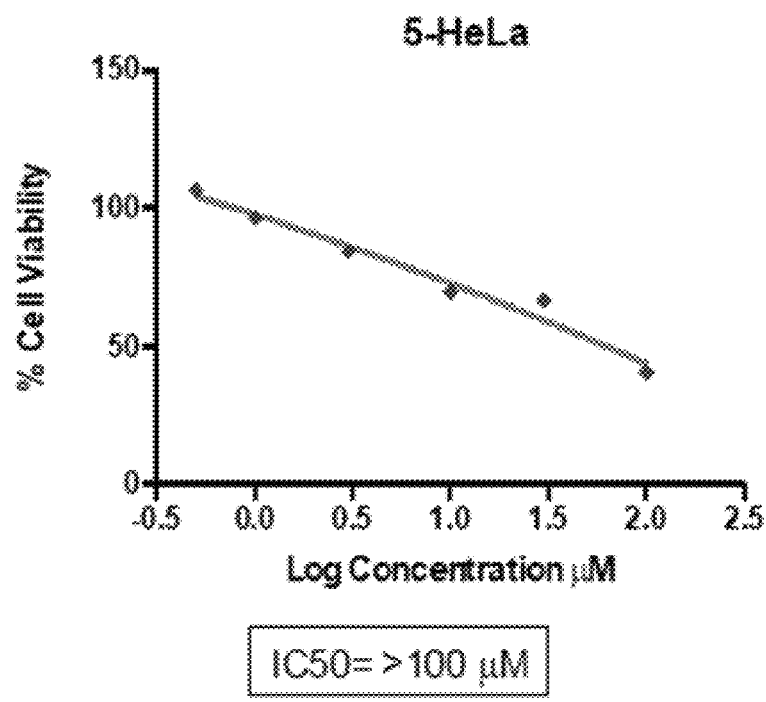
Figure 3F:
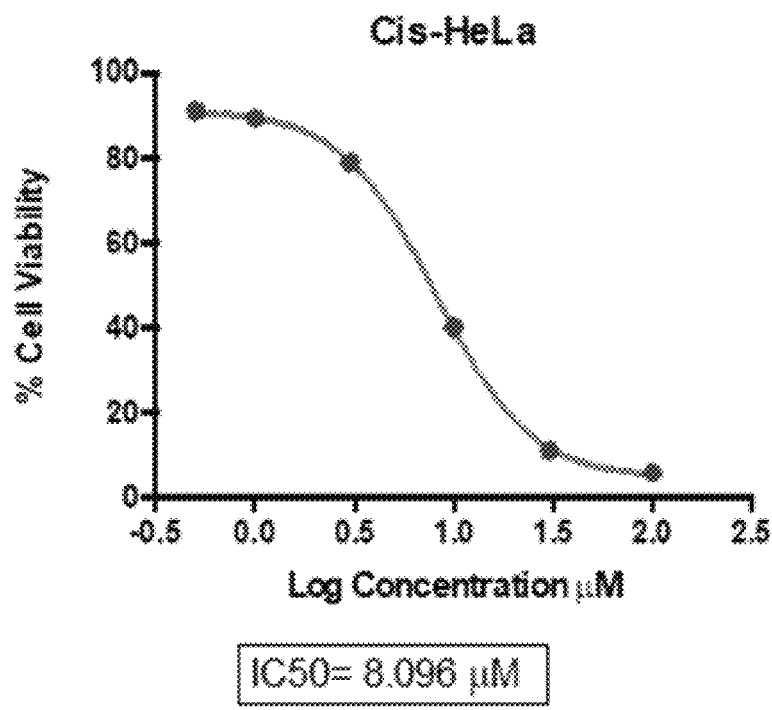
Figure 4:
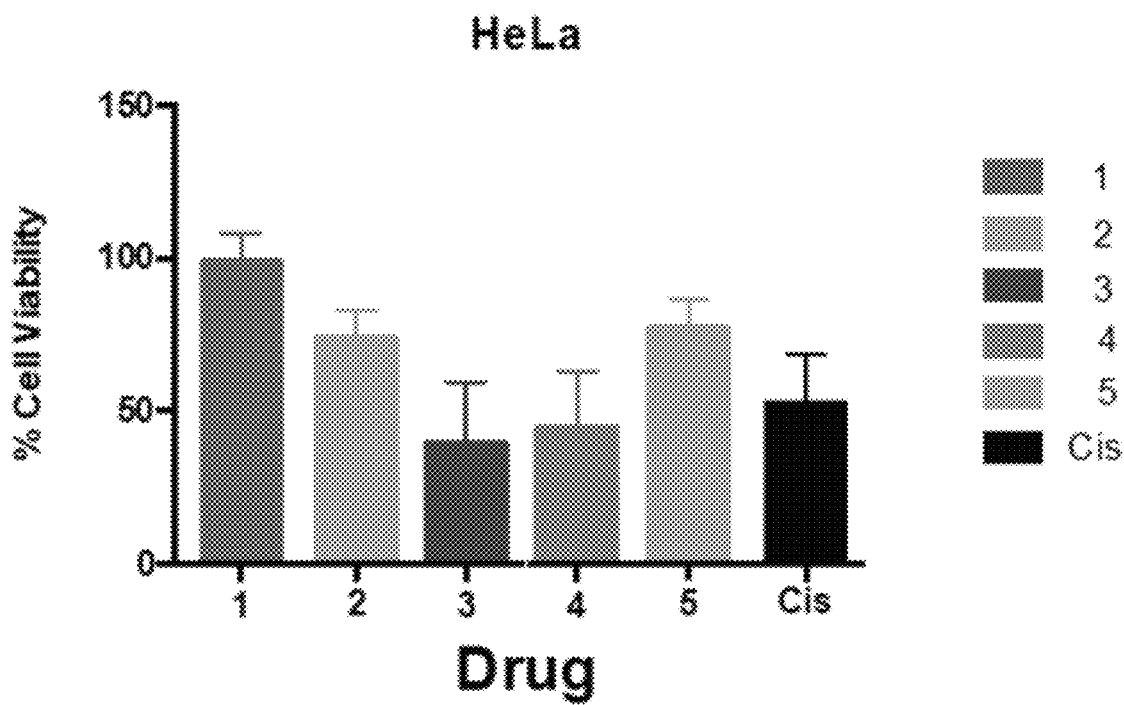
FIG. 4 is a bar graph illustrating the effect of cis-[Pt(NH$_3$)$_2$(selenone)$_2$](NO$_3$)$_2$ complexes (1-5) and cisplatin on the percentage viability of HeLa (cervical cancer cells)
Figure 5A:
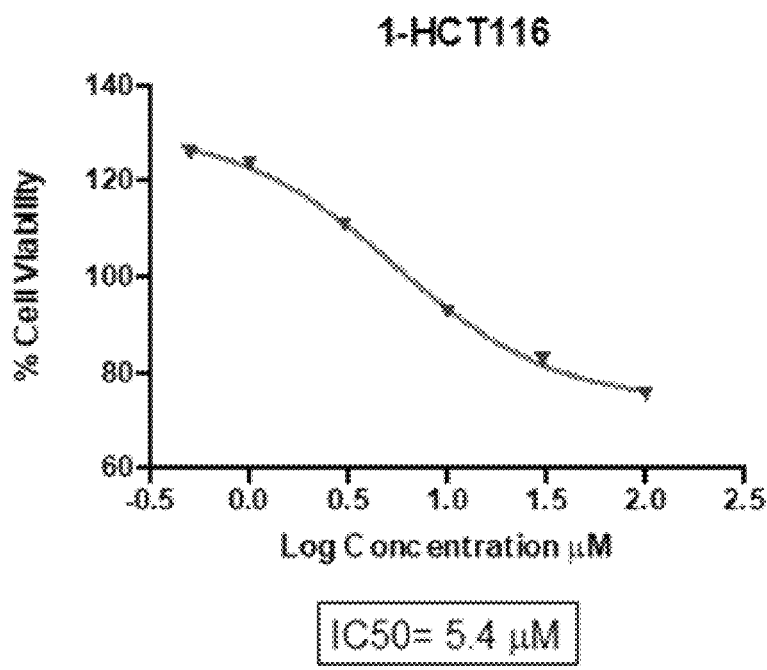
FIGS. 5A-5F are graphs illustrating the effect of concentration of cis-[Pt(NH$_3$)$_2$(selenone)$_2$](NO$_3$)$_2$ complexes 1 (FIG. 5A), 2 (FIG. 5B), 3 (FIG. 5C), 4 (FIG. 5D), 5 (FIG. 5E), and cisplatin ("Cis") (FIG. 5F) on the percentage viability of HCT-116 (colon cancer cells)
Figure 5B:
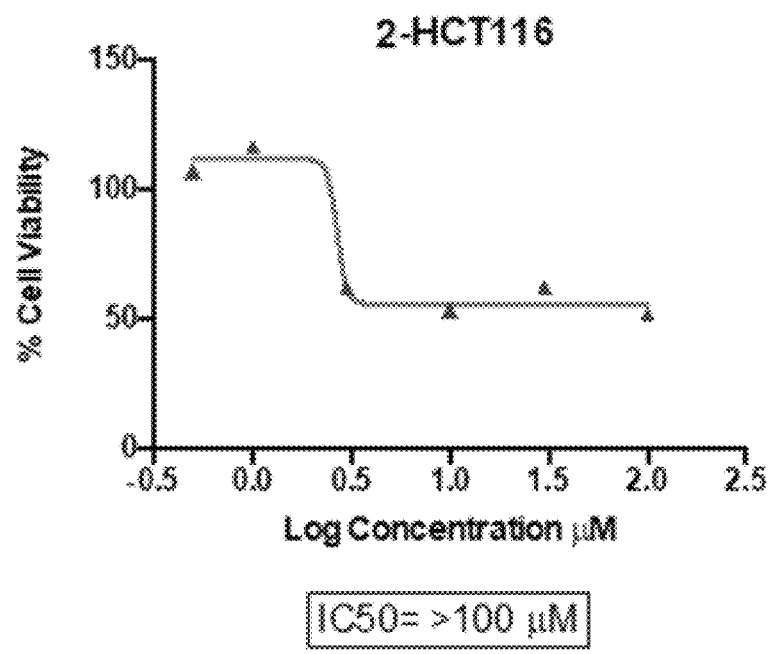
Figure 5C:
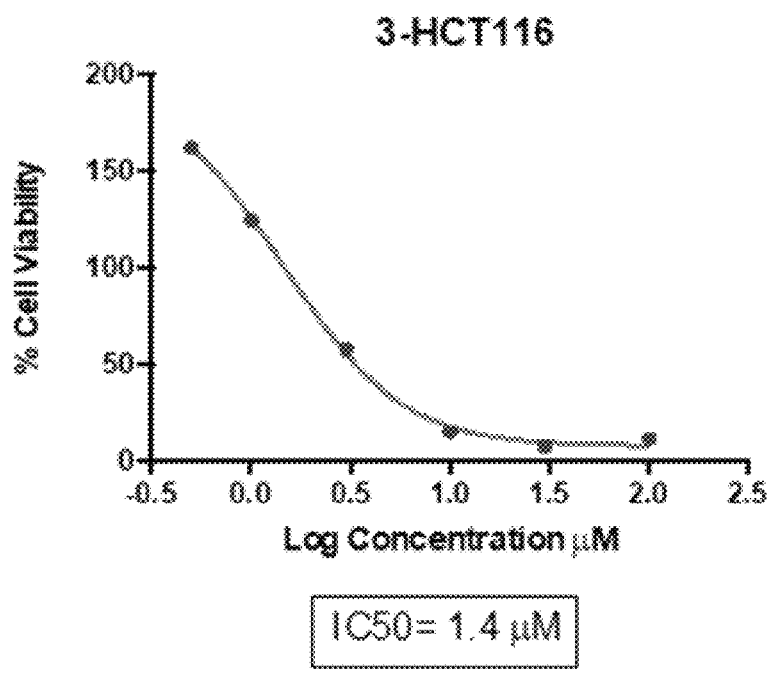
Figure 5D:
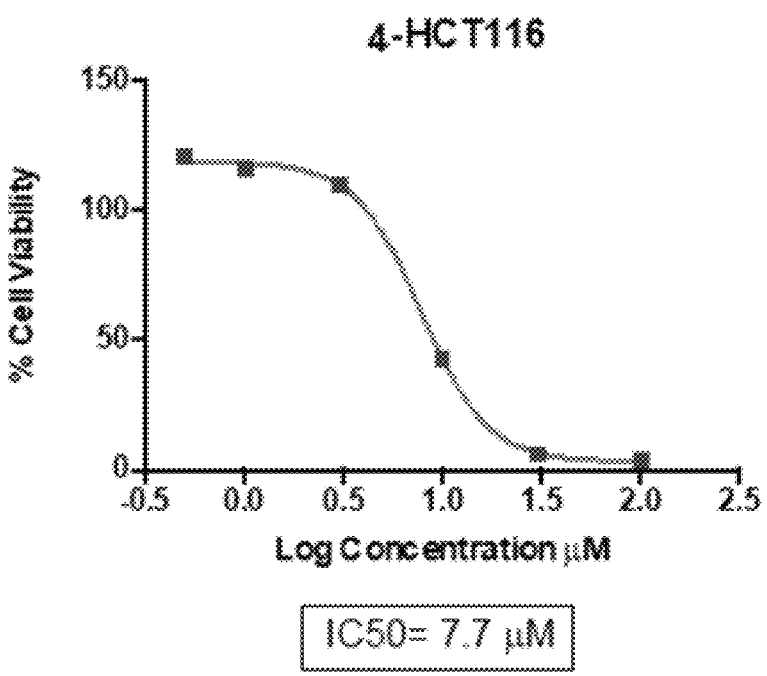
Figure 5E:
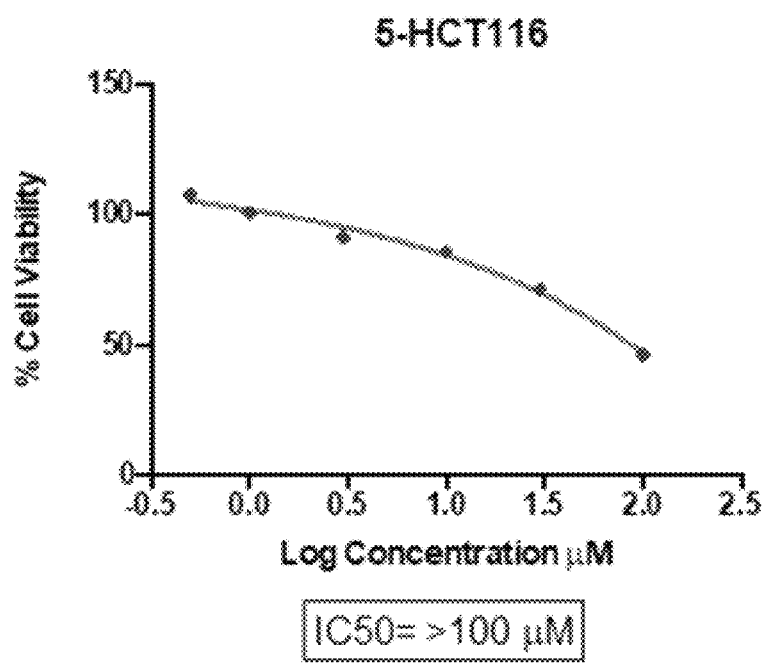
Figure 5F:
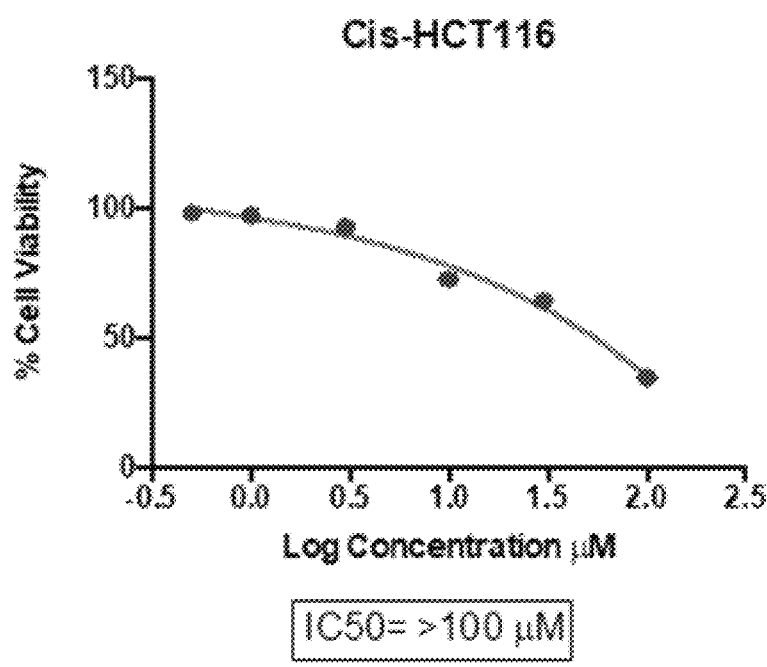
Figure 6:
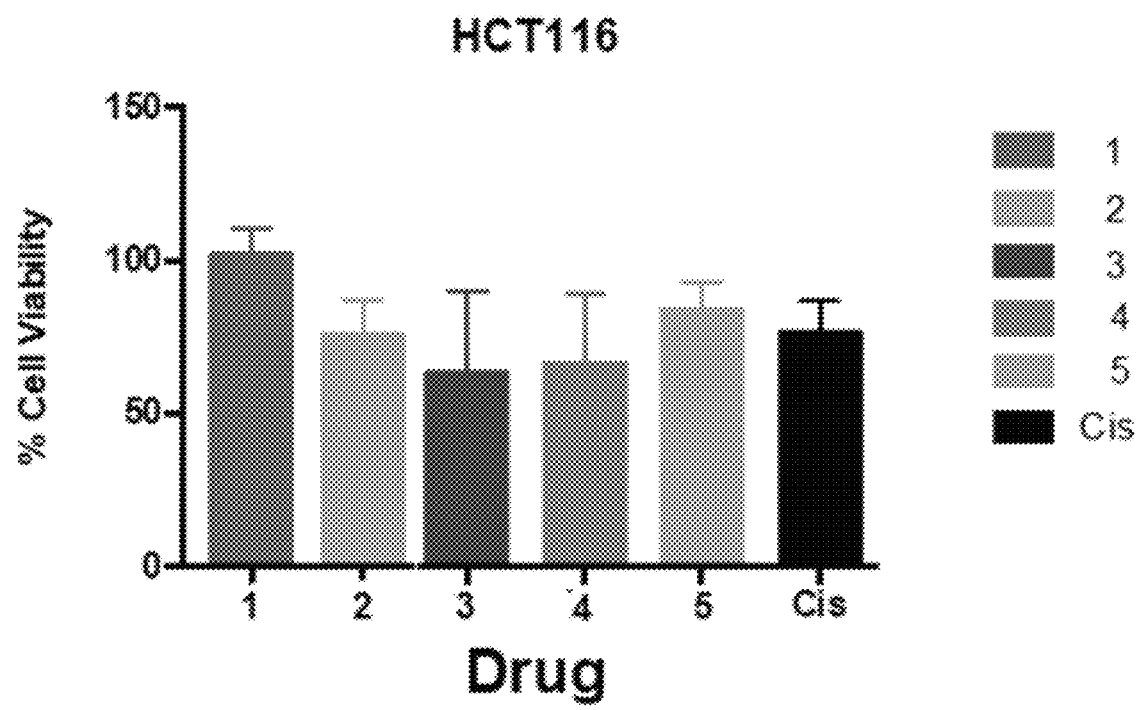
FIG. 6 is a bar graph illustrating the effect of cis-[Pt(NH$_3$)$_2$(selenone)$_2$](NO$_3$)$_2$ complexes (1-5) and cisplatin on the percentage viability of HCT-116 (colon cancer cells)

Embodiments of the present disclosure will now be described more fully hereinafter with reference to the accompanying drawings, in which some, but not all embodiments of the disclosure are shown.

Definitions

As used herein, the terms "compound", "complex", and "product" are used interchangeably, and are intended to refer to a chemical entity, whether in the solid, liquid or gaseous phase, and whether in a crude mixture or purified and isolated.

As used herein, the term "mononuclear" refers to coordination complexes containing a single metal atom (ion) in a single coordination sphere. While the term "binuclear" refers to coordination compounds containing two metal atoms (ions) in a single coordination sphere. The two atoms may be held together through direct metal-metal bonds, through bridging ligands, or both.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the disclosure. Many geometric isomers of C=C double bonds, C=N double bonds, ring systems, and the like can also be present in the complexes, and all such stable isomers are contemplated in the present disclosure. Cis- and trans- (or E- and Z-) geometric isomers of the complexes of the present disclosure are described and may be isolated as a mixture of isomers or as separated isomeric forms. The present complexes can be isolated in optically active or racemic forms. Optically active forms may be prepared by resolution of racemic forms or by synthesis from optically active starting materials. All processes used to prepare complexes of the present disclosure and intermediates made therein are considered to be part of the present disclosure. When enantiomeric or diastereomeric products are prepared, they may be separated by conventional methods, for example, by chromatography, fractional crystallization, or through the use of a chiral agent. Depending on the process conditions the end products of the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric complexes of the present disclosure may be separated into the individual isomers. Complexes of the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure. Further, a given chemical formula or name shall encompass all conformers, rotamers, or conformational isomers thereof where such isomers exist. Different conformations can have different energies, can usually interconvert, and are very rarely isolatable. There are some molecules that can be isolated in several conformations. For example, atropisomers are isomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g., polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

The present disclosure is intended to include all isotopes of atoms occurring in the present complexes. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed.

As used herein, "pharmaceutically acceptable salt" refers to derivatives of the disclosed complexes wherein the parent complex is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like. The pharmaceutically acceptable salts of the present disclosure can be synthesized from the parent complex that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 18th Edition, Mack Publishing Company, Easton, Pa. (1990), the disclosure of which is hereby incorporated by reference.

As used herein, the term "alkyl" unless otherwise specified refers to both branched and straight chain aliphatic (non-aromatic) hydrocarbons which may be primary, secondary, and/or tertiary hydrocarbons typically having 1 to 32 carbon atoms (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, etc.) and specifically includes, but is not limited to, saturated alkyl groups such as methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, tetradecyl, pentadecyl, hexadecyl, heptadecyl, octadecyl, nonadecyl, eicosyl, guerbet-type alkyl groups (e.g., 2-methylpentyl, 2-ethylhexyl, 2-proylheptyl, 2-butyloctyl, 2-pentylnonyl, 2-hexyldecyl, 2-heptylundecyl, 2-octylodecyl, 2-nonyltridecyl, 2-decyltetradecyl, and 2-undecylpentadecyl), as well as unsaturated alkenyl and alkynyl variants such as vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, oleyl, linoleyl, and the like.

The term "cycloalkyl" refers to cyclized alkyl groups. Exemplary cycloalkyl groups include, but are not limited to, saturated cycloalkyl groups such as cyclopropyl, cyclobutyl, cyclopentyl, cyclohexyl, norbornyl, and adamantyl, branched cycloalkyl groups such as 1-methylcyclopropyl and 2-methylcyclopropyl, and cycloalkenyl groups such as cyclobutenyl, cyclopentenyl, and cyclohexenyl.

The term "aryl" means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, anthracenyl, indanyl, 1-naphthyl, 2-naphthyl, and tetrahydronaphthyl. The fused aryls may be connected to another group either at a suitable position on the cycloalkyl/cycloalkenyl ring or the aromatic ring.

The term "arylalkyl", as used herein, refers to a straight or branched chain alkyl moiety (as defined above) that is substituted by an aryl group (as defined above), examples of which include, but are not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "alkoxy" refers to an —O-alkyl group. Example alkoxy groups include, but are not limited to, methoxy, ethoxy, propoxy (e.g., n-propoxy and isopropoxy), and t-butoxy.

As used herein, the term "heterocycle" or "heterocyclyl" is intended to mean a stable 3-, 4-, 5-, 6-, or 7-membered monocyclic, 7-, 8-, 9-, 10-, or 11-membered bicyclic, or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any bicyclic or polycyclic group in which any of the above-defined heterocyclic rings is fused to a carbocyclic ring, the carbocyclic ring being either saturated, unsaturated, or aromatic (e.g., a benzene ring). The nitrogen and sulfur heteroatoms may optionally be oxidized (i.e., N→0 and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include "heteroaryl" (which will be defined below).

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furyl, furazanyl, imidazolidinyl, imidazolinyl, imidazolyl, 1H-indazolyl, imidazolopyridinyl, indolenyl, indolinyl, indolizinyl, indolyl (e.g., 1H-indolyl), isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, homopiperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles. Examples of 5- to 10-membered heterocycles include, but are not limited to, pyridinyl, thienyl, pyrrolyl, furyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, IH-indazolyl, benzofuranyl, benzothiofuranyl, benztetrazolyl, benzo triazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heterocycles include, but are not limited to, pyridinyl, furyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles. Examples of a bicyclic heterocyclic group include, but are not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydroquinoxalinyl, and 1,2,3,4-tetrahydro-quinazolinyl.

The term "heteroaryl" is intended to mean stable monocyclic and polycyclic aromatic hydrocarbons that include at least one heteroatom ring member such as sulfur, oxygen, or nitrogen. Heteroaryl groups are heterocyclyl groups which are aromatic, and may include, without limitation, pyridyl, pyrrolyl, pyrimidinyl, pyrazinyl, pyridazinyl, triazinyl, furyl, quinolyl, isoquinolyl, thienyl, imidazolyl, thiazolyl, indolyl (e.g., 1H-indolyl), pyrroyl, oxazolyl, benzofuryl, benzothienyl, benzthiazolyl, isoxazolyl, pyrazolyl, triazolyl, tetrazolyl, indazolyl (e.g., 1H-indazolyl), 1,2,4-thiadiazolyl, isothiazolyl, purinyl, carbazolyl, benzimidazolyl, indolinyl, benzodioxolanyl, and benzodioxane. Heteroaryl groups may be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→0 and $S(O)_p$, wherein p is 0, 1 or 2).

The term "halo" or "halogen" includes fluoro, chloro, bromo and iodo.

As used herein, the term "substituted" refers to at least one hydrogen atom that is replaced with a non-hydrogen group, provided that normal valencies are maintained and that the substitution results in a stable compound. When a group is noted as "optionally substituted", the group may or may not contain non-hydrogen substituents. When present, the substituent(s) may be selected from alkyl, halo (e.g., chloro, bromo, iodo, fluoro), hydroxyl, alkoxy, oxo, alkanoyl, aryloxy, alkanoyloxy, amino (—$NH_2$), alkylamino (—NHalkyl), cycloalkylamino (—NHcycloalkyl), arylamino (—NHaryl), arylalkylamino (—NHarylalkyl), disubstituted amino (e.g., in which the two amino substituents are selected from alkyl, aryl or arylalkyl, including substituted variants thereof, with specific mention being made to dimethylamino), alkanoylamino, aroylamino, arylalkanoylamino, thiol, alkylthio, arylthio, arylalkylthio, alkylthiono, arylthiono, arylalkylthiono, alkylsulfonyl, arylsulfonyl, arylalkylsulfonyl, sulfonamide (e.g., —$SO_2NH_2$), substituted sulfonamide (e.g., —$SO_2$NHalkyl, —$SO_2$NHaryl, —$SO_2$NHarylalkyl, or cases where there are two substituents on one nitrogen selected from alkyl, aryl, or alkylalkyl), nitro, cyano, carboxy, unsubstituted amide (i.e. —$CONH_2$), substituted amide (e.g., —CONHalkyl, —CONHaryl, —CONHarylalkyl or cases where there are two substituents on one nitrogen selected from alkyl, aryl, or alkylalkyl), alkoxycarbonyl, aryl, guanidine, heterocyclyl (e.g., pyridyl, furyl, morpholinyl, pyrrolidinyl, piperazinyl, indolyl, imidazolyl, thienyl, thiazolyl, pyrrolidyl, pyrimidyl, piperidinyl, homopiperazinyl), and mixtures thereof. The substituents may themselves be optionally substituted, and may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

Platinum(II) Complexes

The present disclosure provides mononuclear cationic platinum(II) complexes having medicinal or pharmaceutical properties, preferably antitumor or anticancer properties. In these platinum(II) complexes, the central platinum(II) atom is coordinated in a mixed ligand environment, preferably by (i) ammonia ligands and (ii) selenourea ligands (sometimes referred to herein as "selenone" ligands since the ligands contain a carbonyl-type structure whereby the oxygen is replaced with a selenium atom). The generic structure of selenourea is shown below:

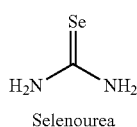

Selenourea

Because the platinum(II) complexes of the present disclosure include coordinating ammonia ligand(s), the complexes may be classified as metal ammine complexes, specifically platinum ammine complexes.

The platinum(II) complex of the present disclosure preferably has four ligands within the coordination sphere of the metal, and adopts a square planar geometry or a distorted square planar geometry. In preferred embodiments, each of these four ligands are neutral ligands (i.e., there are no anionic ligands such as chloro ligands within the coordination sphere of the metal), making the platinum(II) complex cationic, preferably divalent cationic (with the central platinum atom carrying a +2 charge), with charge balancing anions located outside the coordination sphere of the metal to balance the overall charge of the complex. Like ammonia ligands, which can only coordinate in a monodentate fashion, the coordination of each selenourea ligand to the platinum(II) atoms is preferably in mornodentate manner. In some embodiments, the platinum(II) complex is mononuclear (i.e., contains one platinum(II) atom), with two ammonia ligands and two selenourea ligands coordinated to the platinum(II) atom in a monodentate fashion. It is preferred that the platinum(II) complex adopts a cis-configuration, i.e., is a cis-platinum(II) complex, whereby the two ammonia ligands (and the two selenourea ligands) are located in adjacent coordinating positions, akin to cisplatin.

Platinum(II) Complex of Formula (I)

In a first aspect, the present disclosure provides a platinum (II) complex of formula (I),

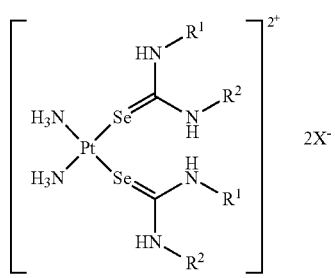

or a pharmaceutically acceptable solvate or tautomer thereof, wherein:

$R^1$ and $R^2$ are each independently a hydrogen, an optionally substituted alkyl, an optionally substituted cycloalkyl, an optionally substituted arylalkyl, or an optionally substituted aryl; or wherein $R^1$ and $R^2$ together form a five-, six-, or seven-membered ring with the nitrogen atoms to which they are attached; and X is a nitrate anion, a hexafluorophosphate anion, a hexafluoroantimonate anion, a trifluoromethanesulfonate anion, a tetrafluoroborate anion, a perchlorate anion, or a halide anion.

In terms of $R^1$ and $R^2$, these substituents may be the same or different. Preferably $R^1$ and $R^2$ are the same. In some embodiments, $R^1$ and $R^2$ are each independently hydrogen, an optionally substituted alkyl, or an optionally substituted arylalkyl, preferably $R^1$ and $R^2$ are each independently hydrogen or an optionally substituted alkyl. Preferred alkyl groups are $C_1$ to $C_8$ alkyl groups, preferably $C_1$ to $C_7$ alkyl groups, preferably $C_1$ to $C_6$ alkyl groups, preferably $C_1$ to $C_5$ alkyl groups, preferably $C_2$ to $C_4$ alkyl groups, which may be substituted or unsubstituted, preferably unsubstituted, with specific mention being made to methyl, ethyl, and propyl.

In some embodiments, $R^1$ and $R^2$ are each hydrogen.

In some embodiments, $R^1$ and $R^2$ are the same, and are each methyl or ethyl, most preferably methyl.

In preferred embodiments, $R^1$ and $R^2$, together with the nitrogen atoms to which they are attached, form a five-membered ring (a 1,3-imidazolidine), a six-membered ring (a 1,3-diazinane), or seven-membered ring (a 1,3-diazepane), the ring being optionally substituted, preferably unsubstituted. For example, $R^1$ and $R^2$ may form a five-, six-, or seven-membered ring with the nitrogen atoms to which they are attached, and thus the selenourea ligands coordinated to the platinum(II) atom may include, but are not limited to, 1,3-imidazolidine-2-selenone, 1,3-diazinane-2-selenone, and 1,3-diazepane-2-selenone, as shown below:

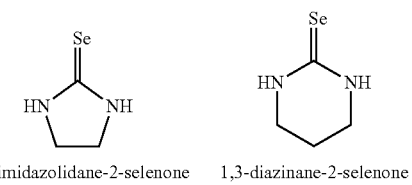

1,3-imidazolidane-2-selenone    1,3-diazinane-2-selenone

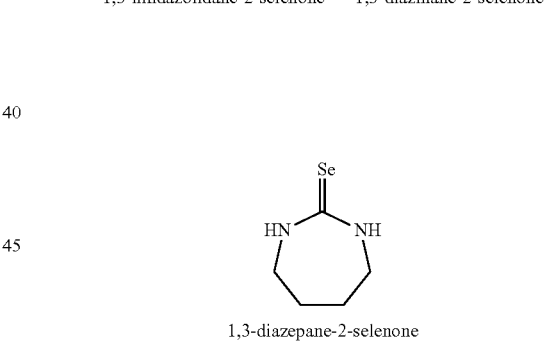

1,3-diazepane-2-selenone

Of these ring sizes, the five- and six-membered ring sizes are preferred, with the five-membered ring sizes being the most preferred.

In the platinum(II) complex of formula (I), X represents a counter anion which is outside of the coordination sphere of the complex, i.e., not directly bound to the platinum atom. As the platinum(II) complex of formula (I) is divalent cationic (the central platinum atom carrying a +2 charge), and since the ammonia and selenourea-type ligands are neutral ligands, the platinum(II) complex of formula (I) includes two $X^-$ counter anions to balance the charge. X may be a nitrate anion, a hexafluorophosphate anion, a hexafluoroantimonate anion, a trifluoromethanesulfonate anion, a tetrafluoroborate anion, a perchlorate anion, or a halide anion such as chloro, bromo, iodo, or fluoro. In preferred embodiments, X is a nitrate anion ($NO_3^-$).

Preferred platinum(II) complexes of the present disclosure are selected from the group consisting of

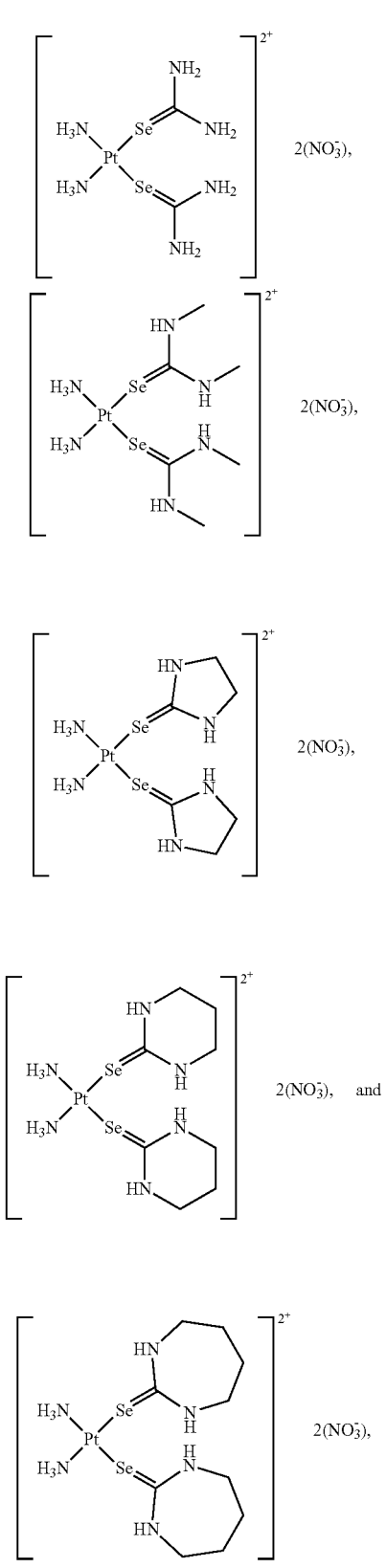

with the most preferred being

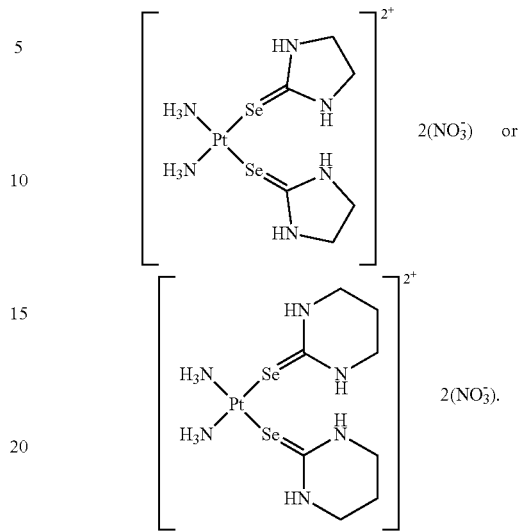

Methods of Making

The platinum(II) complexes of formula (I) may be prepared by various complexation or ligand exchange methods, which are generally known to those of ordinary skill in the art. The following method set forth below is provided for illustrative purposes and is not intended to limit the scope of the disclosure.

The platinum(II) complexes may, for example, be synthesized according to a ligand exchange route starting from cisplatin (cis-diamminedichloridoplatinum(II)). Briefly, cisplatin may be transmetalated with a silver(I) salt to remove and replace the chlorido ligands with more labile ligands such as nitrato ligands. Examples of silver(I) salts which may be used herein include, but are not limited to, silver(I) nitrate, silver(I) heptafluorobutyrate, silver(I) hexafluorophosphate, silver(I) hexafluoroantimonate, silver(I) trifluoromethanesulfonate, silver(I) tetrafluoroborate, and silver(I) perchlorate. A mole ratio of the silver(I) salt to the cisplatin may be in a range of 1:1 to 5:1, preferably 1.2:1 to 4.5:1, preferably 1.4:1 to 4:1, preferably 1.6:1 to 3.5:1, preferably 1.8:1 to 3:1, preferably 2:1 to 2.5:1.

Transmetallation with the silver(I) salt may be performed using one or more organic solvents, including, but not limited to, aromatic solvents (e.g., benzene, ethylbenzene, o-xylene, m-xylene, p-xylene, and mixtures of xylenes, toluene, mesitylene, anisole, 1,2-dimethoxybenzene, α,α,α,-trifluoromethylbenzene, fluorobenzene, heavy aromatic naptha), alkane solvents (e.g., pentane, cyclopentane, hexanes, cyclohexane, heptanes, cycloheptane, octanes), ethers (e.g. diethyl ether, tetrahydrofuran, 1,4-dioxane, tetrahydropyran, t-butyl methyl ether, cyclopentyl methyl ether, di-isopropyl ether), glycol ethers (e.g. 1,2-dimethoxyethane, diglyme, triglyme), chlorinated solvents (e.g. chlorobenzene, dichloromethane, 1,2-dichloroethane, 1,1-dichloroethane, chloroform, carbon tetrachloride), ester solvents (e.g. ethyl acetate, propyl acetate), ketones (e.g. acetone, butanone), formamides/acetamides (e.g., formamide, dimethyl formamide, dimethyl acetamide), monoalcohols (e.g., methanol, ethanol, propanol, isopropanol, n-butanol, isobutanol, n-pentanol, n-hexanol, terpineol, menthol, prenol, 3-methyl-3-buten-1-ol, 2-ethyl-1-hexanol, 2-ethyl-1-butanol, 2-propylheptan-1-ol, 2-butyl-1-octanol, benzyl alcohol), polyalcohols including glycols (e.g., ethylene glycol, diethylene glycol, triethylene glycol, tetraethylene glycol, propylene glycol, dipropylene glycol, 1,3-propanediol, 1,3-butanediol, 1,4-butanediol, 1,6-hexanediol, glycerol, pentaerythritol, manitol, sorbitol), nitromethane, acetonitrile, as well as mixtures thereof. Preferably, the transmetallation reaction is run in ethanol for solvent, and may be performed for 0.1 to 10 hours, 0.5 to 6 hours, or 1 to 3 hours with optional agitation (e.g., using an agitator, a vortexer, a rotary shaker, a magnetic stirrer, a centrifugal mixer, an overhead stirrer, etc.).

Transmetallation of cisplatin with a silver(I) salt produces a transmetalated platinum(II) ammine complex having two ammonia ligands and two labile ligands derived from the anion of the silver(I) salt employed (e.g., nitrato ligands in the case where silver(I) nitrate is employed), along with silver(I) chloride as byproduct, which is preferably removed prior to selenourea ligand addition. Any solid-liquid separation technique may be employed for the removal of silver(I) chloride, such as filtration, decantation, and centrifugation, just to name a few.

Next, an appropriate selenourea ligand(s) is added to the transmetalated platinum(II) ammine complex. For example, a selenourea ligand of formula (II) may be added

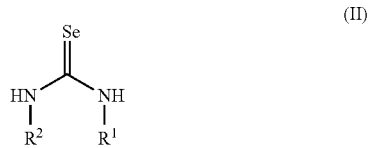

(II)

where $R^1$ and $R^2$ are as defined previously, including where $R^1$ and $R^2$ together form a five-, six-, or seven-membered ring with the nitrogen atoms to which they are attached. Suitable examples of the selenourea ligand of formula (II) include, but are not limited to, selenourea ($SeC(NH_2)_2$), N,N'-dimethylselenourea, N,N'-diethylselenourea, N,N'-dipropylselenourea, N-methylselenourea, N-cyclohexyl,N'-methylselenourea, 1,3-imidazolidine-2-selenone, 1,3-diazinane-2-selenone, and 1,3-diazepane-2-selenone, including mixtures thereof.

The selenourea ligand(s) may be added to the transmetalated platinum(II) ammine complex as a solution in an appropriate organic solvent, such as one or more organic solvents listed previously, with specific mention being made to ethanol and acetonitrile. The addition may be performed batch wise or dropwise, preferably dropwise. In some embodiments, a concentration of the selenourea ligand in the organic solvent may range from 0.01 to 1 M, preferably 0.04 to 0.8 M, preferably 0.06 to 0.6 M, preferably 0.08 to 0.4 M, preferably 0.1 to 0.2 M. A mole ratio of the selenourea ligand to the transmetalated platinum(II) ammine complex may be in a range of 2:1 to 5:1, preferably 2.2:1 to 4.5:1, preferably 2.4:1 to 4:1, preferably 2.6:1 to 3.5:1, preferably 2.8:1 to 3:1. The reaction mixture may be agitated for 0.1 to 10 hours, 0.5 to 6 hours, or 1 to 3 hours to form the platinum(II) complex (es) of the present disclosure.

The platinum(II) complex of the present disclosure may be isolated/purified by methods known to those of ordinary skill in the art, such as one or more of crystallization, precipitation, filtration, solvent evaporation, drying, and the like.

Of course, it should be understood that the platinum(II) complexes may be synthesized through various other synthetic schemes, reactions types and conditions, and isolation/purification procedures and still be considered a part of the present disclosure.

Pharmaceutical Compositions

The present disclosure relates to a pharmaceutical composition which comprises a therapeutically effective amount of one or more of the platinum(II) complexes, formulated together with one or more pharmaceutically acceptable carriers and/or excipients, and optionally, one or more additional therapeutic agents. As described in detail below, the pharmaceutical compositions of the present disclosure may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous, epidural injection, or intratumoral, as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds/complexes, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, a "composition" or a "pharmaceutical composition" refers to a mixture of an active ingredient(s) with other chemical components, such as pharmaceutically acceptable carriers and/or excipients. One purpose of a composition is to facilitate administration of the platinum(II) complexes disclosed herein in any of their embodiments to a subject. Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes. Depending on the intended mode of administration (e.g., oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient" or "active compound", as used herein, refers to an ingredient in the composition that is biologically active, for example, one or more of the platinum(II) complexes. In some embodiments, additional therapeutic agents, in addition to the platinum(II) complexes of the current disclosure, may be incorporated into a pharmaceutical composition, for example, a second active ingredient which is chemically distinct from the platinum(II) complexes.

When the platinum(II) complexes are administered as pharmaceuticals, to humans and animals, they can be given per se or as a pharmaceutical composition containing the active ingredient(s) in combination with a pharmaceutically acceptable carrier and/or excipient. The pharmaceutical composition may contain, for example, up to 99.9 wt. %, preferably up to 99 wt. %, preferably up to 90 wt. %, preferably up to 80 wt. %, preferably up to 70 wt. %, preferably up to 60 wt. %, preferably up to 50 wt. %, preferably up to 40 wt. %, preferably up to 30 wt. %, preferably up to 20 wt. %, preferably up to 10 wt. %, preferably up to 5 wt. %, preferably up to 1 wt. %, preferably up to 0.5 wt. %, preferably up to 0.1 wt. %, preferably up to 0.01 wt. %, preferably up to 0.001 wt. %, preferably up to 0.0001 wt. %, of the platinum(II) complex, based on a total weight of the pharmaceutical composition. For example, when formulated as a solution, the pharmaceutical composition may contain 0.1 to 100 µM, preferably 0.5 to 80 µM, preferably 0.8 to 60 µM, preferably 1 to 40 µM, preferably 2 to 30 µM, preferably 3 to 25 µM, preferably 4 to 20 µM, preferably 5 to 15 µM, preferably 6 to 12 µM, preferably 7 to 11 µM of the platinum(II) complex relative to a total volume of the pharmaceutical composition.

In some embodiments, the active ingredient of the current disclosure, e.g., the platinum(II) complexes, a solvate thereof, a tautomer thereof, or any mixtures thereof, may provide utility as an anticancer agent in reducing the viability of cancer cells derived from human cancer cell lines including, but not limited to, breast cancer cell lines (e.g., MDA-MB-231, MCF-7, SK-BR-3, T47D, VP303); stomach cancer cell lines (e.g., N87, SNU-16, SNU-5, SNU-1, KATO III, AGS); colon/colorectal cancer cell lines (e.g., HCT-116, CACO-2, HT-29, HCT15, MDST8, GP5d, DLD1, SW620, SW403, T84); leukemia cell lines (e.g., HL-60, CESS, CCRF-CEM, CEM/C1, KASUMI-1, ARH-77); liver cancer cell lines (e.g., HepG2, PLC/PRF/5, THLE-3, C3A, SNU-182, SNU-398, SNU-387, SNU-423, SNU-475, SNU-449, and Hep 3B2.1-7); lung cancer cell lines (e.g., A549, NCI-H460, SHP-77, COR-L23/R, NCI-H69/LX20); brain tumor cell lines (e.g., U251); ovarian cancer cell lines (e.g., NCI-ADR/RES, OVCAR-03, A2780, A2780cis, OV7, PEO23); prostate cancer cell lines (e.g., DU145, PC-3); renal cancer cell lines (e.g., 786-0); skin cancer or melanoma cell lines (e.g., UACC-62, C32TG, A375, MCC26), bone cancers such as osteosarcoma cell lines (e.g., MG-63), and cervical cancer cell lines (e.g., HeLa, ME-180, R-ME-180). Preferably, the active ingredient of the current disclosure, e.g., the platinum(II) complexes, a solvate thereof, a tautomer thereof, or any mixtures thereof, provides utility as an anticancer agent in reducing the viability of cancer cells derived from lung cancer cell lines (e.g., A549, NCI-H460, SHP-77, COR-L23/R, NCI-H69/LX20), cervical cancer cell lines (e.g., HeLa, ME-180, R-ME-180), and colon/colorectal cancer cell lines (e.g., HCT-116, CACO-2, HT-29, HCT15, MDST8, GP5d, DLD1, SW620, SW403, T84).

In preferred embodiments, the active ingredient of the current disclosure, e.g., the platinum(II) complexes, a solvate thereof, a tautomer thereof, or any mixtures thereof, may provide utility as an anticancer agent in reducing the viability of cancer cells derived from human cancer cell lines which are resistant to, or which are susceptible to becoming resistant to, other therapeutic agents/chemotherapy agents such as cisplatin and doxorubicin, with specific mention being made to cisplatin resistant cervical cancers (e.g., R-ME-180).

In some embodiments, the cancer cells are collected from a human patient who is at risk of having, is suspected of having, has been diagnosed with, or is being monitored for recurrence of at least one type of cancer, preferably at least one of lung cancer, colon cancer, and cervical cancer.

In some embodiments, the ability of the active ingredient to reduce the viability of cancer cells may be determined by contacting the pharmaceutical composition with the cancer cells and then performing cell viability assays. Methods of such assays include, but are not limited to, sulforhodamine-B (SRB) assay, ATP test, Calcein AM assay, clonogenic assay, ethidium homodimer assay, Evans blue assay, 2',7'-dichlorofluorescin diacetate (DCFDA) or 2',7'-dichlorodihydrofluorescein diacetate (H2DCFDA) staining assay, fluorescein diacetate hydrolysis/propidium iodide staining assay, annexin V/fluorescein isothiocyanate (FITC)/propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, 4',6'-diamidino-2-phenylindole (DAPI) assay, TUNEL assay, a fluorochrome-labeled inhibitors of caspases (FLICA)-based assay, primary (1°) colonosphere formation assay, thioredoxin reductase assay, 20S proteasome activity assay, in vitro scratch assay (for cell migration analysis).

As is well understood in the art, the $IC_{50}$ value of a compound/mixture is a concentration of that compound/mixture which causes the death of 50% of the cellular population to which the compound/mixture is added. In some embodiments, the $IC_{50}$ of the platinum(II) complexes against lung cancer, colon cancer, and cervical cancer cells, is less than 200 µM, preferably less than 150 µM, preferably less than 100 µM, preferably less than 90 µM, preferably less than 80 µM, preferably less than 70 µM, preferably less than 60 µM, preferably less than 50 µM, preferably less than 40 µM, preferably less than 30 µM, preferably less than 25 µM, preferably less than 20 µM, preferably less than 15 µM, preferably less than 10 µM, preferably less than 5 µM, preferably less than 4 µM, preferably less than 3 µM, preferably less than 2 µM, preferably less than 1 µM, preferably less than 0.9 µM, for example, from 0.5 to 25 µM, preferably from 0.6 to 20 µM, preferably from 0.7 to 15 M, preferably from 0.8 to 13 µM, preferably from 0.85 to 10 µM, preferably from 0.9 to 9 M, preferably from 1 to 8 µM, preferably from 1.1 to 7 µM, preferably from 1.2 to 6 µM, preferably from 1.3 to 5 µM, preferably from 1.4 to 4 µM.

In some embodiments, additional therapeutic agents in addition to the platinum(II) complexes of the current disclosure may be incorporated into the pharmaceutical composition.

In some embodiments, the pharmaceutical composition includes an additional therapeutic agent that is chemically distinct from the platinum(II) complex (e.g., of formula (I)), such as a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

The additional therapeutic agent may be an anticancer agent and may include, but is not limited to, at least one of a mitotic inhibitor; an alkylating agent; an antimetabolite; a cell cycle inhibitor; an enzyme; a topoisomerase inhibitor (e.g., doxorubicin); a biological response modifier; an anti-hormone; a tubulin inhibitor; a tyrosine-kinase inhibitor; an antiangiogenic agent such as MMP-2, MMP-9 and COX-2 inhibitor; an anti-androgen; a platinum coordination complex (cisplatin, oxaliplatin, carboplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary additional therapeutic agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, idarubicin, mitomycin, actinomycin, epirubicin; topoisomerase inhibitors including doxorubicin, irinotecan, mitoxantrone, topotecan, and mixtures thereof.

As used herein, the phrase "pharmaceutically acceptable carrier and/or excipient" means a pharmaceutically acceptable material, composition or vehicle, such as a liquid or solid filler, carrier, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier/excipient must be "acceptable" in the sense of being compatible with the other ingredients of the formulation and not injurious to the patient. Some examples of materials which can serve as pharmaceutically acceptable carriers/excipients include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, castor oil, and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol and/or other organic solvents (e.g., DMSO); (20) pH buffered solutions; (21) polyesters, polycarbonates and/or polyanhydrides; (22) other non-toxic compatible substances employed in pharmaceutical formulations, such as cyclodextrins, liposomes, micelle forming agents, e.g., bile acids, polyethoxylated oils (e.g., polyethoxylated castor oil) just to name a few; including mixtures thereof such as cell culture mediums containing mixtures of sugars (e.g., glucose), amino acids, salts, and vitamins/other nutrients, for example minimal essential medium (MEM), Dulbecco's modified Eagle's medium (DMEM), minimum essential medium Eagle-alpha modification (α-MEM), and Glasgow minimal essential medium (Glasgow's MEM).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Methods of preparing these pharmaceutical compositions include the step of bringing into association the platinum(II) complex with the pharmaceutically acceptable carrier and/or excipient, and, optionally, one or more accessory ingredients. In general, the compositions are prepared by uniformly and intimately bringing into association a platinum(II) complex of the present disclosure with liquid carriers, or finely divided solid carriers, or both, and then, if necessary, shaping the product.

Pharmaceutical compositions of the present disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a platinum(II) complex as an active ingredient. A platinum(II) complex of the present disclosure may also be administered as a bolus, electuary or paste.

In solid dosage forms of the present disclosure for oral administration (capsules, tablets, pills, dragees, powders, granules, troches and the like), the active ingredient is mixed with one or more pharmaceutically acceptable carriers and/or excipients, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants (e.g., fatty acid esters of sorbitan and polyalkolyated fatty acid esters of sorbitan such as TWEEN 80, available from Sigma-Aldrich); (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent. The tablets, and other solid dosage forms of the pharmaceutical compositions of the present disclosure may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the Pt(II) complexes of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compound, may contain suspending agents as, for example, ethoxylated isostearyl alcohols, polyoxyethylene sorbitol and sorbitan esters (including polyoxyethylene fatty acid esters of sorbitan, e.g., TWEEN 80), microcrystalline cellulose, aluminum metahydroxide, bentonite, agar-agar and tragacanth, and mixtures thereof. In preferred embodiments, the pharmaceutical composition is in the form of a suspension, comprising, consisting of, or consisting essentially of the platinum(II) complex and the pharmaceutically acceptable carrier and/or excipient, which is preferably a suspending agent (preferably a polyoxyethylene sorbitan ester, preferably a polyoxyethylene fatty acid ester of sorbitan, e.g., TWEEN 80) in an inert diluent (preferably water). Preferably the content of the suspending agent in the suspension ranges from 0.01 to 1 wt. %, preferably 0.05 to 0.8 wt. %, preferably 0.1 to 0.6 wt. %, preferably 0.5 wt. %, based on a total weight of the suspension.

Formulations of the pharmaceutical compositions of the disclosure for rectal or vaginal administration may be presented as a suppository, which may be prepared by mixing one or more platinum(II) complexes with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound(s).

Formulations of the pharmaceutical compositions which are suitable for vaginal administration also include pessaries, tampons, creams, gels, pastes, foams or spray formulations containing such carriers as are known in the art to be appropriate.

Dosage forms for the topical or transdermal administration of a platinum(II) complex of this disclosure include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active platinum(II) complex of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a platinum (II) complex of this disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a platinum(II) complex of the present disclosure to the body. Such dosage forms can be made by dissolving or dispersing the platinum(II) complex in the proper medium. Absorption enhancers can also be used to increase the flux of the platinum(II) complex across the skin. The rate of such flux can be controlled by either providing a rate controlling membrane or dispersing the platinum(II) complex in a polymer matrix or gel.

Ophthalmic formulations, eye ointments, powders, solutions and the like, are also contemplated as being within the scope of this disclosure.

Pharmaceutical compositions of this disclosure suitable for parenteral administration comprise one or more platinum (II) complexes of the present disclosure in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, amino acids, vitamins, alcohols, antioxidants, buffers (e.g., phosphate buffered saline, PBS), bacteriostats, solvents (e.g., DMSO), polyalkoxylated oils such as polyethoxylated castor oil (e.g., CREMOPHOR from Sigma-Aldrich), solutes which render the formulation isotonic with the blood of the intended recipient or suspending or thickening agents.

Examples of suitable aqueous and non-aqueous carriers which may be employed in the pharmaceutical compositions of the disclosure include water, ethanol, DMSO, polyols (such as glycerol, propylene glycol, polyethylene glycol, and the like), vegetable oils such as olive oil, injectable organic esters such as ethyl oleate, nutrient/culture mediums such as those containing mixtures of sugars (e.g., glucose), amino acids, salts, and vitamins/other nutrients, for example minimal essential medium (MEM), Dulbecco's modified Eagle's medium (DMEM), minimum essential medium Eagle-alpha modification (α-MEM), and Glasgow minimal essential medium (Glasgow's MEM), as well as suitable mixtures thereof. Proper fluidity can be maintained, for example, by the use of coating materials, such as lecithin, by the maintenance of the required particle size in the case of dispersions, and by the use of surfactants (e.g., TWEEN 80).

These compositions may also contain adjuvants such as preservatives, wetting agents, emulsifying agents and dispersing agents. Prevention of the action of microorganisms upon the subject platinum(II) complexes may be ensured by the inclusion of various antibacterial and antifungal agents, for example, paraben, chlorobutanol, phenol sorbic acid, and the like. It may also be desirable to include isotonic agents, such as sugars, sodium chloride, and the like into the pharmaceutical compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject platinum(II) complexes in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions which are compatible with body tissue.

In preferred embodiments, the pharmaceutical compositions of this disclosure are formulated for parenteral administration, preferably intratumoral injection, preferably intratumoral injection using a pharmaceutically acceptable carrier and/or excipient made of dimethyl sulfoxide (DMSO) and Dulbecco's modified Eagle's medium (DMEM). For example, the pharmaceutically acceptable carrier and/or excipient may be a mixture of DMSO and DMEM in a volume ratio of 90/10 to 10/90, or 80/20 to 20/80, or 70/30 to 30/70, or 60/40 to 40/60, or 50/50.

In some embodiments, the pharmaceutical composition contains 1 to 99.9999 wt. %, preferably 5 to 99.999 wt. %, preferably 10 to 99.99 wt. %, preferably 15 to 99 wt. %, preferably 20 to 90 wt. %, preferably 30 to 85 wt. %, preferably 40 to 80 wt. %, preferably 50 to 75 wt. % of the pharmaceutically acceptable carrier and/or excipient, relative to a total weight of the pharmaceutical composition.

Therapeutic Applications and Methods

According to another aspect, the present disclosure relates to a method for treating a proliferative disorder such as cancer. The method involves administering a therapeutically effective amount of one or more platinum(II) complexes per se, or a pharmaceutical composition described above to a subject.

In some embodiments, the proliferative disorder is cancer. Types of cancers that may be treated with the platinum(II) complexes of this disclosure include, but are not limited to, brain cancers, skin cancers, bladder cancers, ovarian cancers, breast cancers, gastric cancers, pancreatic cancers, prostate cancers, colon/colorectal cancers, blood cancers, lung cancers, cervical cancers, and bone cancers. In some embodiments, the platinum(II) complexes of this disclosure can be used for the treatment of any cancer type that fails to undergo apoptosis in a patient. This includes, but is not limited to: solid tumors, including but not limited to carcinomas; sarcomas including Kaposi's sarcoma and osteosarcoma; erythroblastoma; glioblastoma; meningioma; astrocytoma; melanoma; and myoblastoma. Treatment or prevention of non-solid tumor cancers, such as leukemia, is also contemplated by this invention.

Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Bur-kitt lymphoma, acute lymphatic leukemia (ALL), chronic lymphatic leukemia (CLL), acute myeloid leukemia (AML), chronic myeloid leukemia (CMIL), adult T-cell leukemia lymphoma, diffuse laige B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma. In preferred embodiments, the cancer is at least one of lung cancer, colon cancer, and cervical cancer.

As used herein, the terms "treat", "treatment", and "treating" in the context of the administration of a therapy to a subject in need thereof refers to the reduction or inhibition of the progression and/or duration of a disease (e.g., cancer), the reduction or amelioration of the severity of the disease, the amelioration of one or more symptoms thereof resulting from the administration of one or more therapies, slowing or arresting disease development, ameliorating the disease, providing relief from the symptoms or side-effects of the disease (including palliative treatment), and causing regression of the disease. Specific to cancer, and in particular, lung, colon, and cervical cancers, these terms may refer to: (1) a stabilization, reduction (e.g., by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g., by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g., colectomy, mastectomy), and (14) preventing or reducing (e.g., by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but not limited to a human, a non-human primate such as a chimpanzee, a domestic livestock such as a cattle, a horse, a swine, a pet animal such as a dog, a cat, and a rabbit, and a laboratory subject such as a rodent, e.g., a rat, a mouse, and a guinea pig. In preferred embodiments, the subject is a human.

The subject may be any subject already with the disease, a subject which does not yet experience or exhibit symptoms of the disease, or a subject predisposed to the disease. In preferred embodiments, the subject is a person who is predisposed to cancer, e.g., a person with a family history of cancer. Women who have (i) certain inherited genes (e.g., mutated BRCA1 and/or mutated BRCA2), (ii) been taking estrogen alone (without progesterone) after menopause for many years (at least 5, at least 7, or at least 10), and/or (iii) been taking fertility drug clomiphene citrate, are at a higher risk of contracting breast cancer. People who (i) consumes a diet high in salty and smoked foods and/or low in fruits and vegetables, (ii) had infection with *Helicobacter pylori*, and/or (iii) long-term stomach inflammation are at a higher risk of contracting stomach cancer. People who (i) had chemotherapy and radiation therapy for other cancers, (ii) has genetic disorders, such as Down syndrome, and/or (iii) exposure to certain chemicals, such as benzene are at a higher risk of contracting leukemia. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. People who have been diagnosed with Human papillomavirus (HPV) are at a higher risk of contracting cervical cancer. Any subject with such predispositions, in combination with sound medical judgment, may be candidates for the treatment methods described herein.

In some embodiments, the subject has leukemia, stomach, colon, testicular, bladder, head and neck cancer, esophageal cancer, mesothelioma, brain, neuroblastoma, bone, lung, prostate, breast, ovarian, and/or cervical cancer and is currently undergoing, or has completed one or more chemotherapy regimens. In some embodiments, the subject has been previously administered/treated with, or is being currently administered/treated with, a thymidylate synthase inhibitor (e.g., capecitabine, fluorouracil (5-FU)), a thymidine phosphorylase (TPase) inhibitor (e.g., tipiracil, trifluridine), a topoisomerase I inhibitor (e.g., irinotecan), a topoisomerase II inhibitor (e.g., doxorubicin), a DNA synthesis inhibitor (e.g., oxaliplatin), a DNA crosslinking agent (e.g., cisplatin), and/or a targeted therapy (e.g., cetuximab, bevacizumab, panitumumab, zivaflibercept, ramucirumab). In some embodiments, the subject has been previously administered/treated with, or is being currently administered/treated with, a tubulin binding drug such as paclitaxel, epothilone, docetaxel, discodermolide, etoposide, vinblastine, vincristine, teniposide, vinorelbine, and vindesine, and developed resistance to the tubulin binding drug. In some embodiments, the subject has been previously administered/treated with, or is being currently administered/treated with, a tyrosine-kinase inhibitor such as imatinib, nilotinib, dasatinib, bosutinib, ponatinib, and bafetinib, and developed drug resistance via (i) Bcr-Abl dependent mechanisms involving Bcr-Abl duplication, Bcr-Abl mutation, T315I mutation, and/or P-loop mutations, or (ii) Bcr-Abl Independent mechanisms involving drug efflux caused by P-glycoproteins, drug import by organic cation transporter 1, and/or alternative signaling pathway activation. In some embodiments, the subject has been previously administered/treated with, or is being currently administered/treated with, a DNA crosslinking agent (e.g., cisplatin) and developed drug resistance via mechanisms related to decreased intracellular uptake, increased reflux, increased inactivation by sulfhydryl molecules such as glutathione, increased excision of the adducts from DNA by repair pathways, increased lesion bypass, and/or altered expression of regulatory proteins involved in signal transduction pathways that control the apoptotic processes. In some embodiments, the subject has been previously administered/treated with, or is being currently administered/treated with, a topoisomerase II inhibitor (e.g., doxorubicin), and developed drug resistance mechanisms via alteration or increased expression of transporters including, but not limited to, one or more of ABCB1 (MDR1, Pgp) and ABCC1 (MRP1), as well as other transporters.

The terms "administer", "administering", "administration", and the like, as used herein, refer to the methods that may be used to enable delivery of the active ingredient and/or the pharmaceutical composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, intratumoral, or infusion), topical and rectal administration. Those of ordinary skill in the art are familiar with administration techniques that can be employed. In preferred embodiments, the active ingredient (e.g., the platinum(II) complexes) or the pharmaceutical composition described herein are administered parenterally, preferably as intratumoral injections, preferably as a sterile isotonic aqueous or non-aqueous solution, dispersion, suspension or emulsion.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", or "pharmaceutically effective amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. Typically, an effective amount of the platinum(II) complex (e.g., to treat cancers such as lung cancer, colon cancer, and cervical cancer, in terms of mg of the platinum(II) complex per body weight of the subject (kg), ranges from 0.01 to 100 mg/kg, preferably 0.05 to 90 mg/kg, preferably 0.1 to 80 mg/kg, preferably 0.5 to 70 mg/kg, preferably 1 to 60 mg/kg, preferably 1.2 to 50 mg/kg, preferably 1.4 to 40 mg/kg, preferably 1.6 to 30 mg/kg, preferably 1.8 to 20 mg/kg, preferably 2 to 10 mg/kg, preferably 2.2 to 5 mg/kg, preferably 2.4 to 3 mg/kg, preferably 2.5 mg/kg.

Platinum(II) complexes of the disclosure may be useful for sensitizing cells to apoptotic signals. Thus, in some embodiments, the platinum(II) complexes of the disclosure are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin ortopotecan; (vii) topoisomerase II poisons, (viii) microtubule-directed agents, (ix) kinase inhibitors (x) miscellaneous investigational agents (xi) hormones, (xii) hormone antagonists, and (xiii) targeted therapies. It is contemplated that platinum(II) complexes of the disclosure may be useful in combination with any known agents falling into the above 13 classes as well as any future agents that are currently in development. In particular, it is contemplated that platinum(II) complexes of the disclosure may be useful in combination with current Standards of Care as well as any that evolve over the foreseeable future. Specific dosages and dosing regimens would be based on physicians' evolving knowledge and the general skill in the art.

Examples of second therapeutic agents include, but are not limited to, a mitotic inhibitor; an alkylating agent; an antimetabolite; a cell cycle inhibitor; an enzyme; a topoisomerase inhibitor; a biological response modifier; an antihormone; a tubulin inhibitor; a tyrosine-kinase inhibitor; an antiangiogenic agent such as MMP-2, MMP-9 and COX-2 inhibitor; an anti-androgen; a platinum coordination complex (oxaliplatin, carboplatin, cisplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane); a thymidylate synthase inhibitor; a thymidine phosphorylase (TPase) inhibitor; a DNA synthesis inhibitor; and/or a targeted therapy. Exemplary second therapeutic agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, doxorubicin, idarubicin, mitomycin, actinomycin, epirubicin; topoisomerase inhibitors including irinotecan, mitoxantrone, topotecan; thymidine phosphorylase (TPase) inhibitors such as tipiracil and trifluridine; DNA synthesis inhibitors such as oxaliplatin; targeted therapies such as cetuximab, bevacizumab, panitumumab, zivaflibercept, ramucirumab; and mixtures thereof.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intratumoral routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Any other administration route combination is also contemplated herein according to the administration routes available for each of the therapeutic agents. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A treatment method may comprise administering the platinum(II) complex or a pharmaceutical composition containing the platinum(II) complex of the current disclosure in any of its embodiments as a single dose or multiple individual divided doses. In some embodiments, the composition is administered at various dosages (e.g., a first dose with an effective amount of 10 mg/kg and a second dose with an effective amount of 2 mg/kg). In some embodiments, the interval of time between the administration of the pharmaceutical composition and the administration of one or more second therapies may be about 1 to 5 minutes, 1 to 30 minutes, 30 minutes to 60 minutes, 1 hour, 1 to 2 hours, 2 to 6 hours, 2 to 12 hours, 12 to 24 hours, 1 to 2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11 to 15 weeks, 15 to 20 weeks, 20 to 30 weeks, 30 to 40 weeks, 40 to 50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, at least 5 days, at least 6 days, or at least 7 days. In some embodiments, the pharmaceutical composition and optionally one or more second therapies are administered less than 1 day, less than 1 week, less than 2 weeks, less than 3 weeks, less than 4 weeks, less than 1 month, less than 2 months, less than 3 months, less than 6 months, less than 1 year, less than 2 years, or less than 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, at least 10%, at least 15%, at least 20%, at least 25%, at least 30%, at least 40%, at least 50%, at least 60%, at least 70%, at least 75%, at least 80%, at least 85%, at least 90%, at least 95%, at least 99%, or 100%, relative to the tumor size before treatment. In some embodiments, the size of a tumor after treatment is not reduced but is maintained at the same size as before treatment. Methods of assessing tumor size include, but are not limited to, CT scan, MRI, DCE-MRI, PET scan, and manual tumor measurements.

The method may further comprise measuring a concentration of a biomarker and/or detecting a mutation in a biomarker before and/or after the pharmaceutical composition comprising the platinum(II) complex of the present disclosure is administered. Generic cancer biomarkers include circulating tumor DNA (ctDNA) and circulating tumor cells (CTC). Exemplary biomarkers for colon cancer include, without limitation, carcinoembryonic antigen (CEA), carbohydrate antigen 242 (CA 242), CA 195, CA 19-9, MSI, and 18qLOH. Exemplary biomarkers for breast cancer include, without limitation, BRCA1, BRCA2, HER-2, estrogen receptor, progesterone receptor, cancer antigen 15-3, cancer antigen 27.29, carcinoembryonic antigen, Ki67, cyclin D1, cyclin E, and ERβ. Exemplary biomarkers for stomach cancer include, without limitation, carcinoembryonic antigen (CEA), CA19-9, carbohydrate antigen (CA) 72-4, alpha-fetoprotein, carbohydrate antigen (CA) 12-5, SLE, BCA-225, hCG, and pepsinogenI/II. Exemplary biomarkers for lung cancer include, without limitation, CYFRA 21-1 (cytokeratins), EPCAM (epithelial cell adhesion molecule), ProGRP (pro-gastrin-releasing peptide), and CEACAM (carcinoembryonic antigen). Exemplary biomarkers for prostate cancer include, without limitation, PSA, hK2/four-kallikrein panel, EN@, Annexin A3, PCA3, and TMPRSS2-ERG. Exemplary biomarkers for ovarian cancer include, without limitation, CEA, cancer antigen 125 (CA125), risk of ovarian malignancy algorithm serum biomarkers (ROMA), human epididymis protein 4 (HE4). Exemplary biomarkers for cervical cancer include, without limitation HPV E6, HPV E7, Mini chromosome maintenance (MCM), Cell division cycle protein 6 (CDC6), p16$^{INK4A}$, Squamous cell carcinoma antigen (SCC), and Ki-67.

Potentially predictive cancer biomarkers include, without limitation, mutations in genes BRCA1 and BRCA2 for breast cancer, overexpressions of TYMS, mutations in genes p53 and KRAS for colon cancer, and high concentration levels of AFP, and overexpressions of HSP90α for liver cancer.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The concentration level of the cancer biomarker in a sample (i.e., biological sample obtained from the subject in need of therapy including a single cell, multiple cells, fragments of cells, a tissue sample, and/or body fluid, for example red blood cells, white blood cells, platelets, hepatocytes, epithelial cells, endothelial cells, a skin biopsy, a mucosa biopsy, an aliquot of urine, saliva, whole blood, serum, plasma, lymph) may be measured for example by an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, a concentration of the biomarker is measured before and after the administration. When the concentration of the biomarker is maintained, the method may further comprise increasing the effective amount of the platinum(II) complex by at least 5%, at least 10%, or at least 30%, and up to 80%, up to 60%, or up to 50% of an initial effective amount. The subject may be administered with the increased dosage for a longer period (e.g., 1 week more, 2 weeks more, or 2 months more) than the duration prescribed with the initial effective amount.

In some embodiments, the administration is stopped once the subject is treated.

The examples below are intended to further illustrate protocols for preparing, characterizing, and using the Pt(II) complexes of the present disclosure, and are not intended to limit the scope of the claims.

Where a numerical limit or range is stated herein, the endpoints are included. Also, all values and subranges within a numerical limit or range are specifically included as if explicitly written out.

The terms "comprise(s)", "include(s)", "having", "has", "can", "contain(s)", and variants thereof, as used herein, are intended to be open-ended transitional phrases, terms, or words that do not preclude the possibility of additional acts or structures. The present disclosure also contemplates other embodiments "comprising", "consisting of" and "consisting essentially of", the embodiments or elements presented herein, whether explicitly set forth or not.

As used herein, the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

EXAMPLES

Experimental Section

Chemicals

Cisplatin (cis-diamminedichloridoplatinum(II)) was obtained from Strem Chemical Company, USA. Dimethyl sulfoxide-d$_6$ was purchased from Fluka Chemical Co. Selenourea and N,N'-dimethylselenourea were obtained from Acros Organics, USA. The other selenone ligands were prepared according to the procedure mentioned in the literature. See Cristiani F, Devillanova F A, Verani G (1977) Infrared study of 1,3-thiazolidin(e)-2-one, -2-thione, and -2-selone and their 1-oxa-analogues. J Chem Soc Perkin Trans 2, 324-327, and Wazeer M I M, Isab A A, Perzanowski H P (2003) Solid-state NMR studies of 1,3-imidazolidine-2-selenone and some related compounds. Magn Reson Chem 41:1026-1029, each incorporated herein by reference in their entirety. (3-(4,5-Dimethylthiazol-2-yl)-2,5-diphenyltetrazolium bromide, a yellow tetrazole) was purchased from Sigma Chemical Co, St. Louis, Mo., USA. Lung cancer (A549), colon cancer (HCT-116) and cervical cancer (HeLa) cell lines were purchased from the American Type Culture Collection, (ATCC, Manassas, Va., USA).

Synthesis of Complexes

The compounds were prepared by adding 0.17 g (1 mmol) of $AgNO_3$ to the solutions containing 0.15 g (0.5 mmol) of cis-diamminedichloridoplatinum(II) (cisplatin) in 10 mL ethanol and stirring the mixture for one hour at room temperature. The solution was filtered to remove silver chloride as solid. Then 1.0 mmol of selenone (selenourea) ligands dissolved in 10 mL ethanol or acetonitrile was added to the filtrates drop wise. Stirring the solutions for two hours resulted in (yellow/brown/gray/white and black) colored solutions. The solutions were filtered and kept at room temperature. Solid powders were isolated on slow evaporation of the solvent. The synthetic procedure can be represented by the following scheme. The elemental (CHN) analysis data of the complexes is given in Table 1.

TABLE 1

Elemental analysis and melting points of cis-diammineplatinum(II) complexes of selenones, cis-[Pt(NH$_3$)$_2$(Selenone)$_2$](NO$_3$)$_2$

| Complex | Found (Calcd) % | | | M.P. (° C.) | Color |
| --- | --- | --- | --- | --- | --- |
| | C | H | N | | |
| [Pt(NH$_3$)$_2$(Seu)$_2$] (NO$_3$)$_2$ (1) | 3.92 (4.01) | 2.40 (2.35) | 18.87 (18.70) | 155-158 | Brown |
| [Pt(NH$_3$)$_2$(Me$_2$Seu)$_2$] (NO$_3$)$_2$ (2) | 10.88 (10.99) | 3.46 (3.38) | 17.27 (17.09) | 140-144 | Gray |
| [Pt(NH$_3$)$_2$(ImSe)$_2$] (NO$_3$)$_2$ (3) | 10.97 (11.06) | 2.93 (2.78) | 16.92 (17.20) | 185-188 | Brown |
| [Pt(NH$_3$)$_2$(DiazSe)$_2$] (NO$_3$)$_2$ (4) | 14.55 (14.41) | 3.39 (3.26) | 16.27 (16.49) | 111-115 | Brown |
| [Pt(NH$_3$)$_2$(DiapSe)$_2$] (NO$_3$)$_2$ (5) | 16.85 (16.97) | 3.88 (3.70) | 15.98 (15.84) | 188-193 | Yellow |

Instrumentation

Elemental analyses were performed on Perkin Elmer Series 11 (CHNS/O), Analyzer 2400. The solid state FTIR spectra were recorded on a Nicolet 6700 FTIR spectrophotometer over the range 4000-400 $cm^1$ at resolution 4.0 $cm^1$. The NMR measurements were carried out in DMSO-$d_6$ on a JEOL JNM-LA 500 NMR spectrometer at 297 K. The $^1$H and proton-decoupled $^{13}$C NMR spectra were recorded at the frequencies of 500.00 MHz and 125.65 MHz respectively. The spectral conditions for $^{13}$C NMR were; 32 K data points, 0.963 s acquisition time, 3.2 s pulse delay and a 5.75 μs pulse width. For $^1$H NMR, 32 K data points, 0.963 s acquisition time, 2.5 s pulse delay and a 5.12 μs pulse width. The chemical shifts were measured relative to TMS. The $^{77}$Se NMR chemical shifts were recorded at 95.35 MHz relative to an external reference ($SeO_2$ in $D_2O$) at 0.00 ppm, using 2.0 s pulse delay and 0.311 s acquisition time.

In Vitro Cytotoxicity of cis-platinum(II) Complexes

The solutions of Pt(II) complexes 1-5 and cisplatin (classical standard control) with 1.0 μM, 5.0 μM, 10.0 μM, 25.0 μM, 50.0 μM and 100.0 μM concentrations were prepared in DMEM. The cancer cells, HeLa (cervical cancer), A549 (Lung cancer) and HCT-116 (colon cancer) were seeded and maintained in quadruplicate in a 96-well tissue culture plate at $5\times10^4$ cells per well in 200 μL of the same medium. The cancer cells were incubated for 24 hours before the treatment. All compounds were dissolved in 50 vol % DMSO (50/50 v/v DMSO/DMEM). Therefore, DMSO was used as a negative control. The final DMSO concentration in each well, was less than 0.1%. The cancer cells were treated with the synthesized complexes (1-5) along with cisplatin and the resultant cultures were incubated for 72 h. The medium of wells was discarded and 100 μL DMEM containing MTT (3-(4,5-dimethylthiazol-2-yl)-2,5-diphenyltetrazolium bromide) (5 mg/mL) was added to the wells and incubated in a $CO_2$ incubator at 37° C. in the dark for 4 hrs. After incubation, a purple colored formazan (artificial chromogenic dye, a product of the reduction of water insoluble tetrazolium salts e.g., MTT by dehydrogenases and reductases) in the cells is produced and appeared as dark crystals in the bottom of the wells. The medium of culture was discarded from each well carefully to avoid disruption of the monolayer. 100 μL of isopropanol was added in each well. The solution was thoroughly mixed in the wells to dissolve the formazan crystals which ultimately results into a purple solution. The absorbance of the 96-well plate was taken at 570 nm with Mithras 2LB943 against reagent blank.

Molecular Docking Study

Molecular docking has become a renowned computational aided drug design tool used in modern drug discovery. See Seliman A A A, Altaf M, Onawole A T, et al (2017) Synthesis, X-ray structures and anticancer activity of gold (I)-carbene complexes with selenones as co-ligands and their molecular docking studies with thioredoxin reductase. J Organomet Chem 848; Seliman A A A, Altaf M, Onawole A T, et al (2017) Synthesis, X-ray structures and anticancer activity of gold(I)-carbene complexes with selenones as co-ligands and their molecular docking studies with thioredoxin reductase. J Organomet Chem 848; Ariöz C, Li Y, Wittung-Stafshede P (2017) The six metal binding domains in human copper transporter, ATP7B: molecular biophysics and disease-causing mutations. BioMetals 30:823-840, each incorporated herein by reference in their entirety. Hence, in an effort towards investigating the mode of interaction of the of newly synthesized cisplatin derived selenone complexes, rigid/flexible molecular docking against a DNA duplex with sequence d(CGCGAATTCGCG)$_2$ dodecamer (PDB ID: 1BNA)(SEQ ID NO:1) was carried out. See Haleel A, Arthi P, Dastagiri Reddy N, et al (2014) DNA binding, molecular docking and apoptotic inducing activity of nickel(ii), copper (ii) and zinc(ii) complexes of pyridine-based tetrazolo[1,5-a]pyrimidine ligands. RSC Adv 4:60816-60830; Dar A M, Uzzaman S, Ahmad M S, Khan Y (2017) Steroidal imidazoles: Synthesis, characterization, molecular docking studies with DNA and in vitro cytotoxicity. Med Chem Res 26:372-383; Jomaa M Y, Ahmad S, Seliman A A A, et al (2019) Synthesis, spectroscopic characterization and in vitro cytotoxic as well as docking studies of cis-diammine platinum(II) complexes of thiones. Inorganica Chim Acta 484: 347-351; and Dickerson R E, Drew H R (1981) Structure of a B-DNA dodecamer. J Mol Biol 149:761-786, each incorporated herein by reference in their entirety. All water molecules were undetached from DNA and polar hydrogen were added to the DNA structure using Discovery Studio program. See BIOVIA (2016) Dassault Systèmes BIOVIA. Dassault Systèmes, incorporated herein by reference in its entirety. Prior to docking, the structures of the newly synthesized cisplatin derived selenone complexes were modeled using molecular modelling software Avagadro 1.2.0. Quantum mechanical geometry optimization of the complexes were performed using Gaussian program. See M J Frisch, G W Trucks, H B Schlegel, G E Scuseria, M A Robb, J R Cheeseman, G Scalmani, V Barone, B Mennucci, G A Petersson, H Nakatsuji, M Caricato, X Li, H P Hratchian, A F Izmaylov, J Bloino, G Zheng, J L Sonnenberg, M Hada, M Ehara, K Toyota, R Fukuda, J Haseg D F (2009) Gaussian 09.6492, incorporated herein by reference in its entirety. The AutoDock Tools (ADT) version 1.5.6 and AutoDock version 4.2.5.1 docking program for the docking of the cisplatin derived selenone complexes to the B-DNA was used. See Morris G M, Goodsell D S, Halliday R S, et al (1998) Automated docking using a Lamarckian genetic algorithm and an empirical binding free energy function. J Comput Chem 19:1639-1662, incorporated herein by reference in its entirety. Kollman charges were used during the docking calculation. Visualization and analysis of the binding mode as well as interactions in the binding pocket of the obtained poses were analyzed using the Discovery Studio program. See Rizvi S M D, Shakil S, Haneef M (2013) A simple click by click protocol to perform docking: Autodock 4.2 made easy for non-bioinformaticians. EXCLI J 12:830-857, incorporated herein by reference in its entirety.

Results and Discussions
Synthesis and Spectroscopic Studies

Cisplatin, cis-[Pt(NH$_3$)$_2$Cl$_2$] was first converted into more reactive nitrato form by addition of AgNO$_3$. The selenones were then added in a molar ratio of 1:2 to yield the desired complexes of the composition, [Pt(NH$_3$)$_2$(Selenone)$_2$](NO$_3$)$_2$. The significant IR bands of the selenones and the platinum (II) complexes are listed in Table 2. The v(C=Se) vibration of the selenones around 600-730 cm$^{-1}$ shifted towards a lower frequency upon complexation as reported earlier. See Ahmad S, Isab A A, Al-Arfaj A R, Arnold A P (2002) Synthesis of cyano(selenone)gold(I) complexes and investigation of their scrambling reactions using 13C and 15N NMR spectroscopy. Polyhedron 21:2099-2105; Ahmad S, Isab A A, Arnold A P (2003) Synthesis and Spectroscopic Characterization of Silver(I) Complexes of Selenones. J Coord Chem 56:539-544; Ahmad S, Altoum A O S, Vančo J, et al (2018) Synthesis, crystal structure and anticancer activity of tetrakis(N-isopropylimidazolidine-2-selenone) platinum(II) chloride. J Mol Struct 1152:232-236; Altoum A O S, Alhoshani A, Alhosaini K, et al (2017a) Synthesis, characterization and in vitro cytotoxicity of platinum(II) complexes of selenones [Pt(selenone)$_2$Cl$_2$]. J Coord Chem 70:1020-1031; Altoum A O S, Vančo J, Křikavová R, et al (2017b) Synthesis, structural characterization and cytotoxicity evaluation of platinum(II) complexes of heterocyclic selenones. Polyhedron 128:2-8; and Alhoshani A, Seliman A A A, Altoum A O, et al (2019) Synthesis, X-ray structure and in vitro cytotoxicity of trans-diammineplatinum(II) complexes of selenones, trans-[Pt(NH$_3$)$_2$(selenone)$_2$](NO$_3$)$_2$. Polyhedron 158:234-240; each incorporated herein by reference in their entirety. The v(N—H) and v(C—N) bands were observed around 3200 cm$^{-1}$ and 1400 cm$^{-1}$ respectively. The signals near 800 and 1300 cm$^{-1}$ mark the presence of nitrate ions. See Isab A A, Ahmad S, Arab M (2002) Synthesis of silver(I) complexes of thiones and their characterization by 13C, 15N and 107Ag NMR spectroscopy. Polyhedron 21:1267-1271; Isab A A, Wazeer M I M, Fettouhi M, et al (2006) Synthesis and characterization of mercury(II) complexes of selones: X-ray structures, CP MAS and solution NMR studies. Polyhedron 25:2629-2636; and Alhoshani A, Seliman A A A, Altoum A O, et al (2019) Synthesis, X-ray structure and in vitro cytotoxicity of trans-diammineplatinum(II) complexes of selenones, trans-[Pt(NH$_3$)$_2$(selenone)$_2$](NO$_3$)$_2$. Polyhedron 158:234-240, each incorporated herein by reference in their entirety.

The $^1$H (N—H protons), $^{13}$C and $^{77}$Se NMR data of the ligands and their complexes in DMSO-d$_6$ are given in Table 3. In H NMR spectra of the complexes, the N—H signal of selenones appeared downfield by about 1.0 ppm with respect to its position in free ligands. The deshielding is due to an increase in π character of the C—N bond upon coordination. The ammonia protons were detected around 4 ppm. In $^{13}$C NMR spectra, an upfield shift in the >C=Se resonance of selenones was observed upon complexation (Table 3). An upfield shift in C-2 resonance indicates the coordination of selenone ligands through the selenium atom. See Ahmad S, Isab A A, Arnold A P (2003) Synthesis and Spectroscopic Characterization of Silver(I) Complexes of Selenones. J Coord Chem 56:539-544; and Alhoshani A, Seliman A A A, Altoum A O, et al (2019) Synthesis, X-ray structure and in vitro cytotoxicity of trans-diammineplatinum(II) complexes of selenones, trans-[Pt(NH$_3$)$_2$(selenone)$_2$](NO$_3$)$_2$. Polyhedron 158:234-240, each incorporated herein by reference in its entirety. The other (C—H) resonances were only slightly shifted. The $^{13}$C NMR spectra of the complexes 1 and 3-5 are given in FIGS. 10-13.

In $^{77}$Se NMR spectra, the selenone signal shifted upfield upon complexation providing clear evidence of selenium binding to the metal center. The DiapSe complex (5) shows the highest shift difference of 84 ppm, suggesting its highest stability among the prepared complexes. The $^{77}$Se NMR spectra of complexes (1-5) are given in FIGS. 14-18.

TABLE 2

Selected IR absorptions (cm$^{-1}$) of selenones and their cis-Pt(II) complexes

| Species | v(C=S) | v(NH) | v(C—N) | v(NO)$_3$ |
|---|---|---|---|---|
| Seu | 736 | 3265 | 1520 | — |
| 1 | 603 | 3320, 3222 | 1410 | 1349 |
| Me2Seu | 730 | 3245 | 1432 | — |
| 2 | 600 | 3355 | 1393 | 1353 |
| ImSe | 561 | 3250 | 1463 | — |
| 3 | 552 | 3283 | 1397 | 1365 |
| DiazSe | 601 | 3200 | 1465 | — |
| 4 | 558 | 3365 | 1411 | 1366 |
| DiapSe | 615 | 3224 | 1453 | — |
| 5 | 600 | 3299 | 1324 | 1396 |

TABLE 3

$^1$H (for N—H proton), $^{13}$C{$^1$H} and $^{77}$Se{$^1$H}NMR chemical shifts of the cis-Pt(II) complexes with selenones in DMSO-d$_6$.

| Species | N—H | C=Se | N-C2 | C3 | δ($^{77}$Se) |
|---|---|---|---|---|---|
| Seu | 7.59 | 178.8 | — | — | 200.7 |
| 1 | 8.53 | 168.0 | — | — | 160.5 |
| Me$_2$Seu | 7.55 | 177.8 | 31.0 | — | 231.4 |
| 2 | 8.39 | 169.5 | 31.5 | — | 185.9 |
| ImSe | 8.33 | 177.1 | 44.9 | — | 73.5 |
| 3 | 9.30 | 167.9 | 45.3 | — | 52.5 |
| DiazSe | 7.13 | 171.0 | 40.8 | 18.9 | 199.9 |
| 4 | 7.97 | 160.4 | 40.2 | 18.4 | 165.5 |
| DiapSe | 8.05 | 180.8 | 45.5 | 26.5 | 292.0 |
| 5 | 8.96 | 171.6 | 46.3 | 26.0 | 175.9 |

In Vitro Cytotoxicity

The in vitro cytotoxicity of the prepared compounds (1-5) and cisplatin in DMSO was examined by the MTT assay against three human cancer cells namely, HeLa (cervical cancer cells), A549 (lung cancer cells) and HCT-116 (colon cancer cells). The results of cytotoxicity in terms of IC$_{50}$ value are presented in Table 4. The survival of the cells as a function of concentration of compounds 1-5 (and compared to cisplatin) is shown in FIGS. 1A-1F, 2, 3A-3F, 4, 5A-5F, and 6. Two complexes, 3 and 4 have in vitro cytotoxicity higher than cisplatin for all cells, while complex 1 has activity against HCT-116 only. Complex 2 exhibits cytotoxicity comparable to cisplatin for HeLa cells, while for the other two cell lines, it is almost inactive. Complex 5 was found ineffective against all three cells, while 1 shows no activity for HeLa and A549 cells. Complex 3 of the present series possesses the highest activity among all the selenone complexes reported to date by the inventors. See Altoum A O S, Alhoshani A, Alhosaini K, et al (2017a) Synthesis, characterization and in vitro cytotoxicity of platinum(II) complexes of selenones [Pt(selenone)$_2$Cl$_2$]. J Coord Chem 70:1020-1031; Altoum A O S, Vančo J, Křikavová R, et al (2017b) Synthesis, structural characterization and cytotoxicity evaluation of platinum(II) complexes of heterocyclic selenones. Polyhedron 128:2-8; Ahmad S, Altoum A O S, Vančo J, et al (2018) Synthesis, crystal structure and anticancer activity of tetrakis(N-isopropylimidazolidine-2-selenone)platinum(II) chloride. J Mol Struct 1152:232-236; and Alhoshani A, Seliman A A A, Altoum A O, et al (2019) Synthesis, X-ray structure and in vitro cytotoxicity of trans-diammineplatinum(II) complexes of selenones, trans-[Pt(NH$_3$)$_2$(selenone)$_2$](NO$_3$)$_2$. Polyhedron 158:234-240, each incorporated herein by reference in their entirety. The more effective antitumor properties of the current series may be ascribed to the presence of ammine groups at the cis position and to their ionic nature.

TABLE 4

IC$_{50}$ values (μM) of cis-platinum(II) complexes (1-5) against HeLa, A549, and HCT-116 cancer cell lines

| Complex | A549 | HeLa | HCT-116 |
| --- | --- | --- | --- |
| Cisplatin | 12.52 (±0.02) | 8.096 (±0.049) | >100 |
| 1 | >100 | >100 | 5.4 (±0.05) |
| 2 | 54.02 (±0.03) | 12.2 (±0.05) | >100 |
| 3 | 1.2 (±0.03) | 0.895 (±0.062) | 1.4 (±0.063) |
| 4 | 6.74 (±0.05) | 3.7 (±0.05) | 7.7 (±0.05) |
| 5 | >100 | >100 | >100 |

Molecular Docking

Figure 7A:
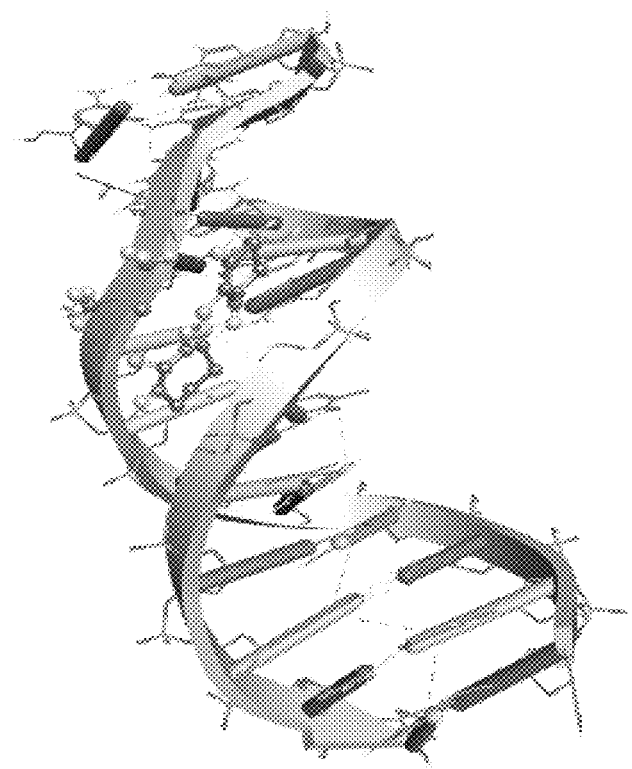
FIGS. 7A-7C illustrate the docking analysis of Complex 5 with B-DNA, where
Figure 7B:
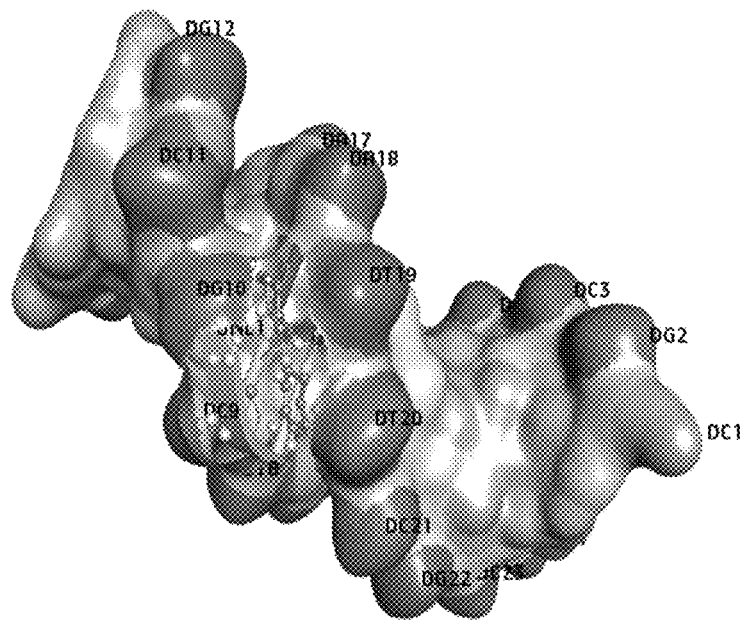
Figure 7C:
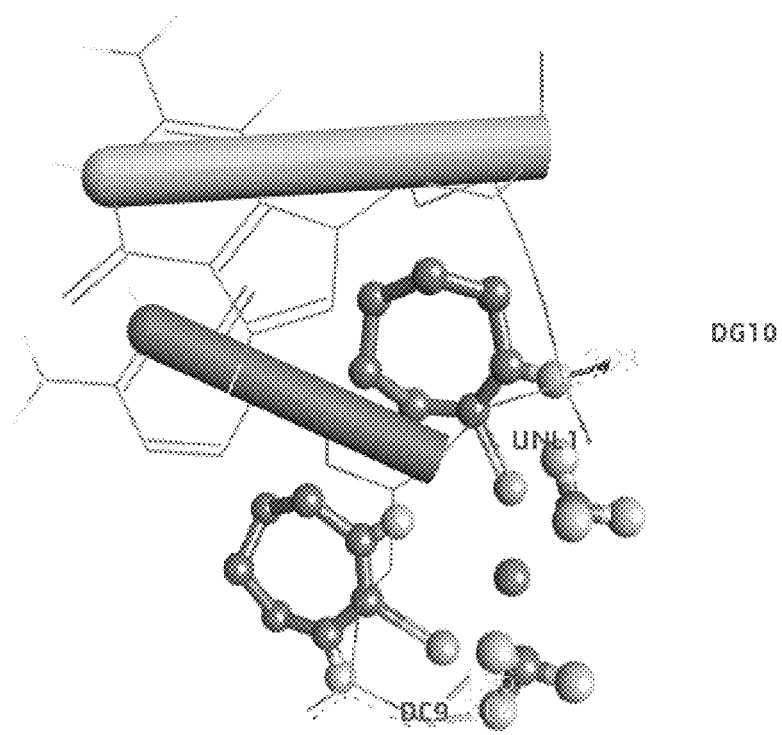
Figure 8:
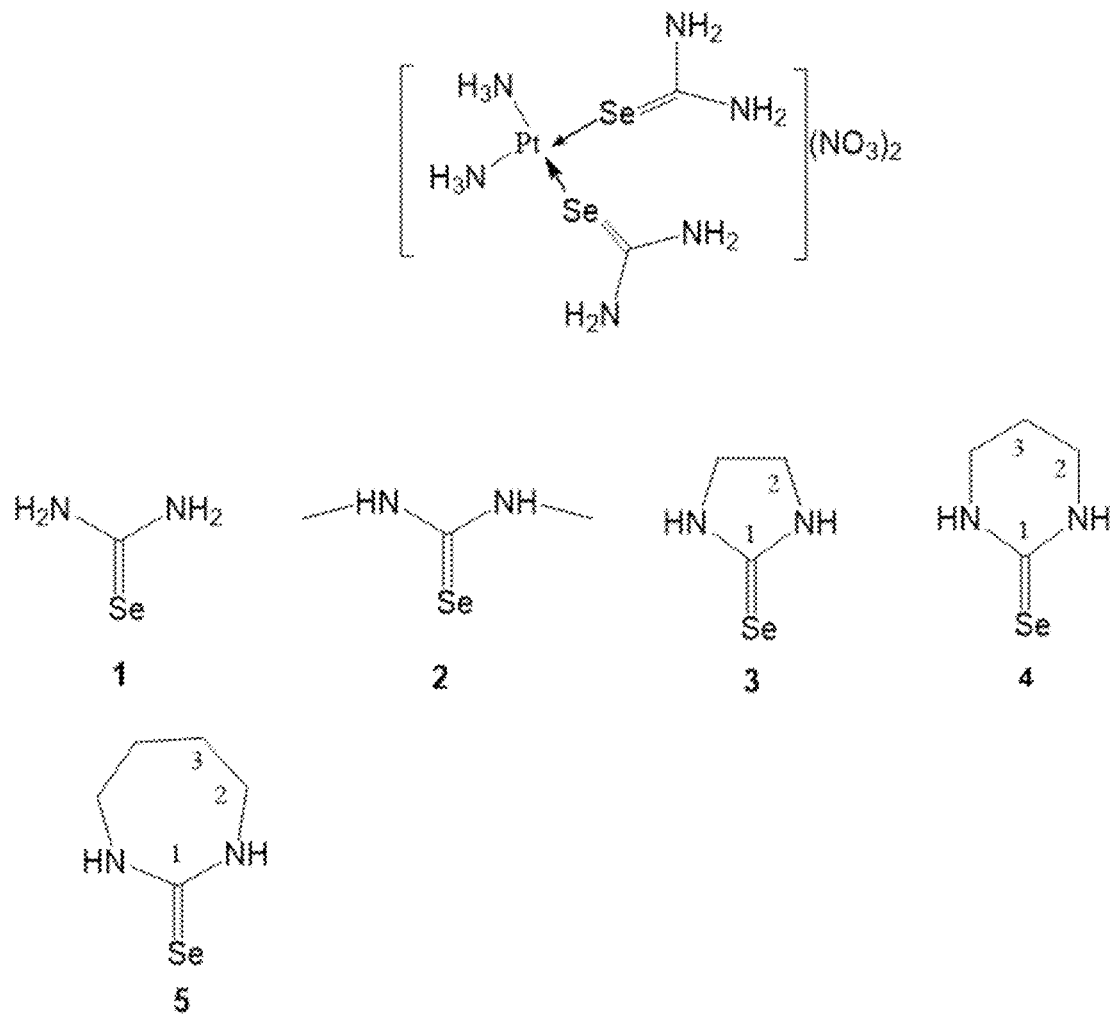
FIG. 8 illustrates structures of the selenourea complexes (also referred to as selenone complexes) used in the study.
Figure 9:
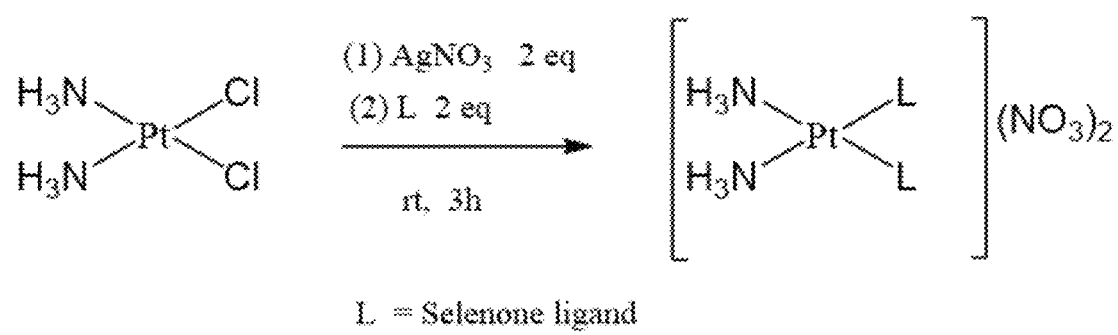
FIG. 9 depicts the synthesis route used to form the complexes starting from cisplatin.
Figure 10:
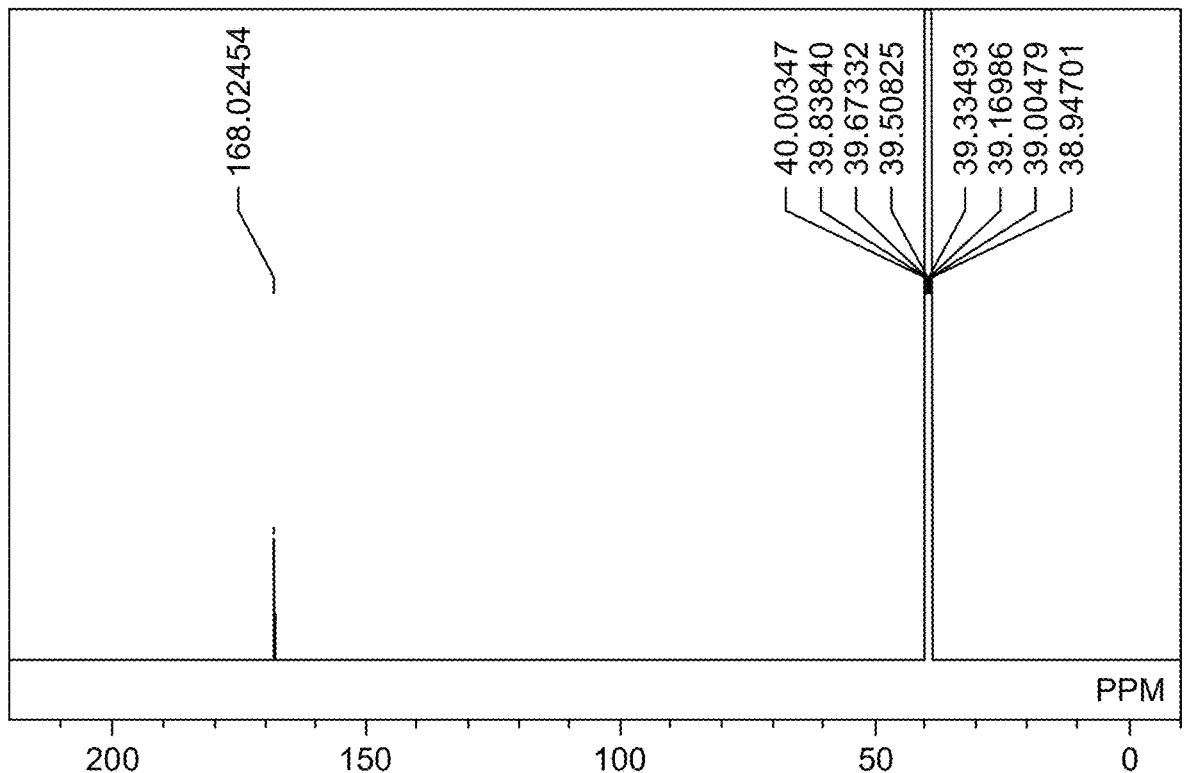
FIG. 10 is a graph illustrating $^{13}$C NMR spectrum of complex 1 in DMSO-d$_6$.
Figure 11:
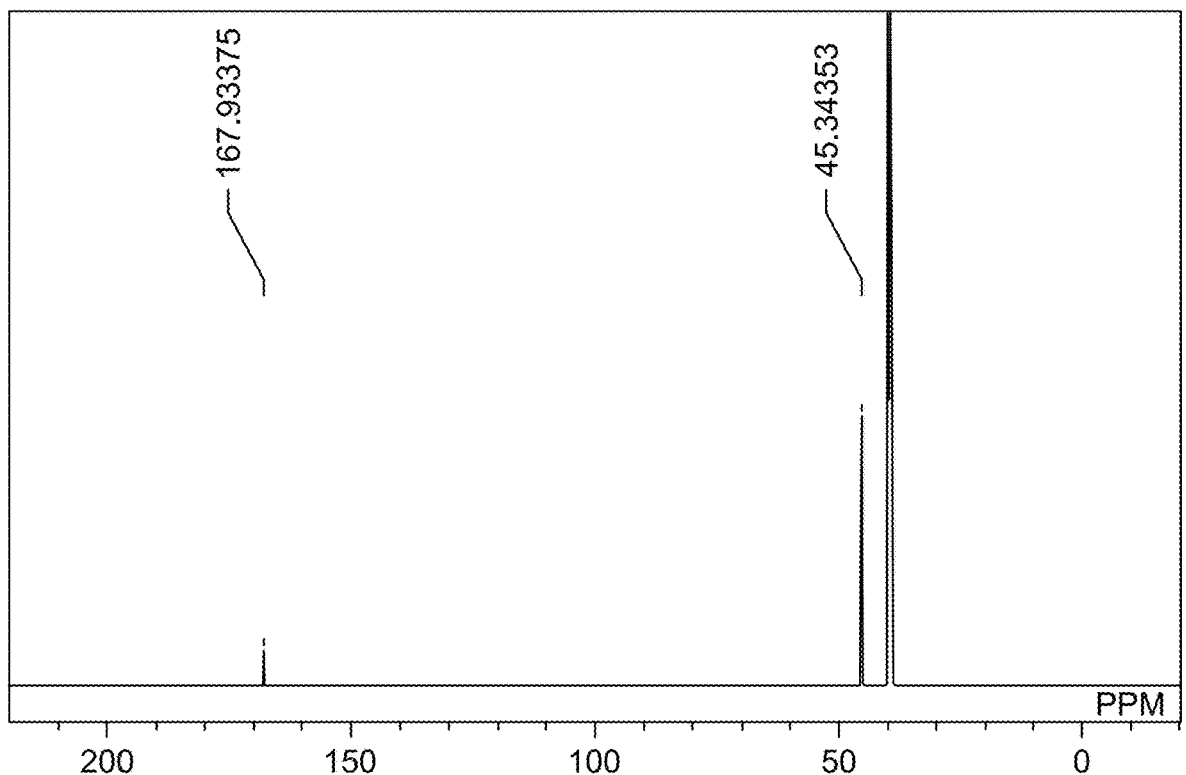
FIG. 11 is a graph illustrating $^{13}$C NMR spectrum of complex 3 in DMSO-d$_6$.
Figure 12:
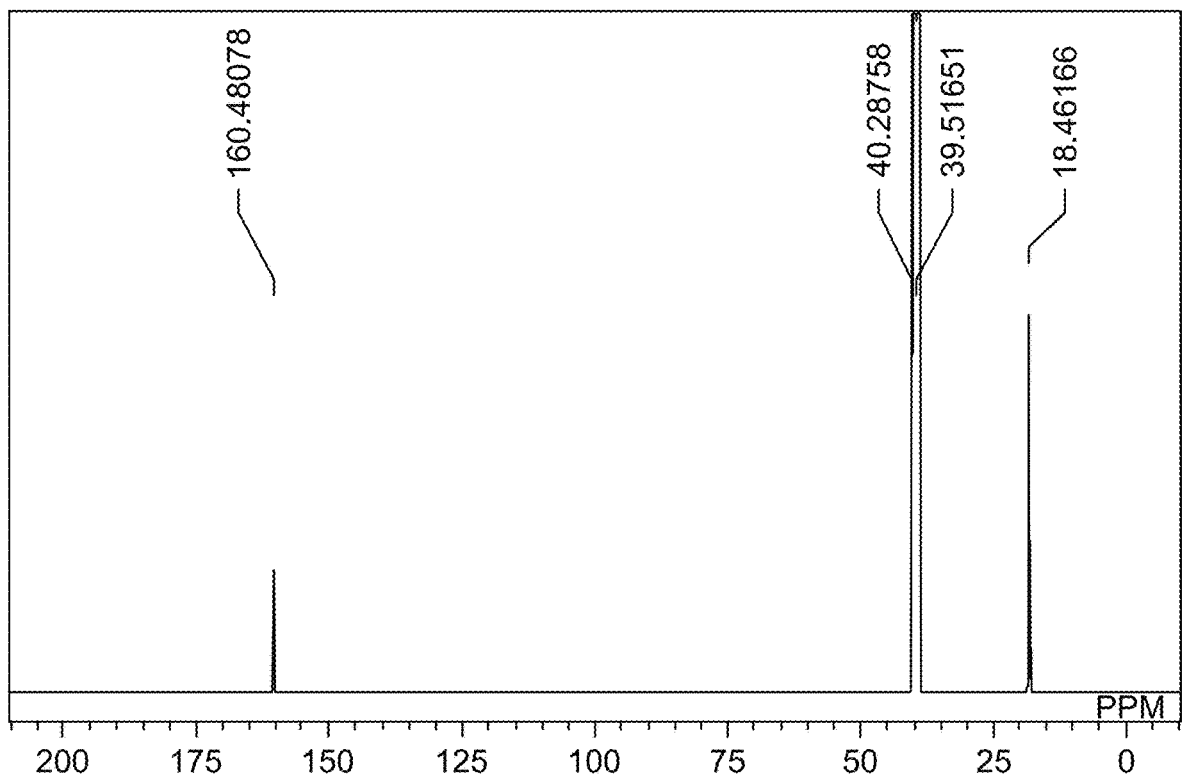
FIG. 12 is a graph illustrating $^{13}$C NMR spectrum of complex 4 in DMSO-d$_6$.
Figure 13:
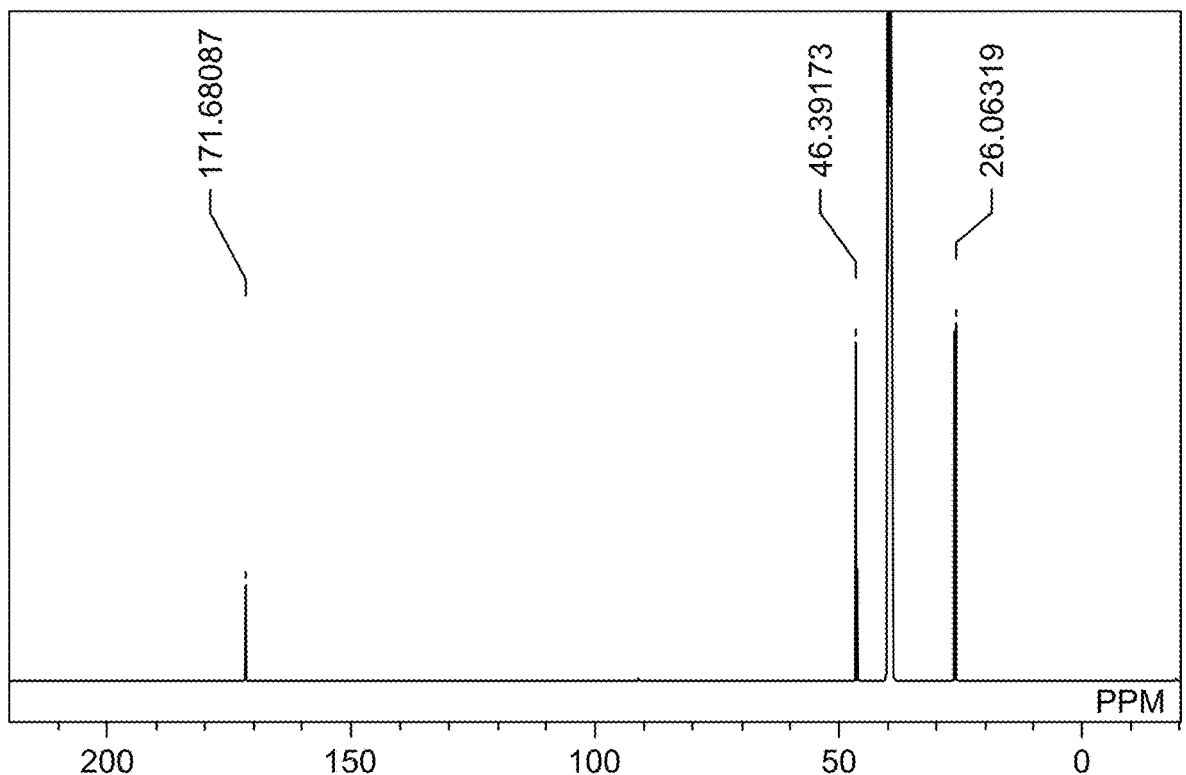
FIG. 13 is a graph illustrating $^{13}$C NMR spectrum of complex 5 in DMSO-d$_6$.
Figure 14:
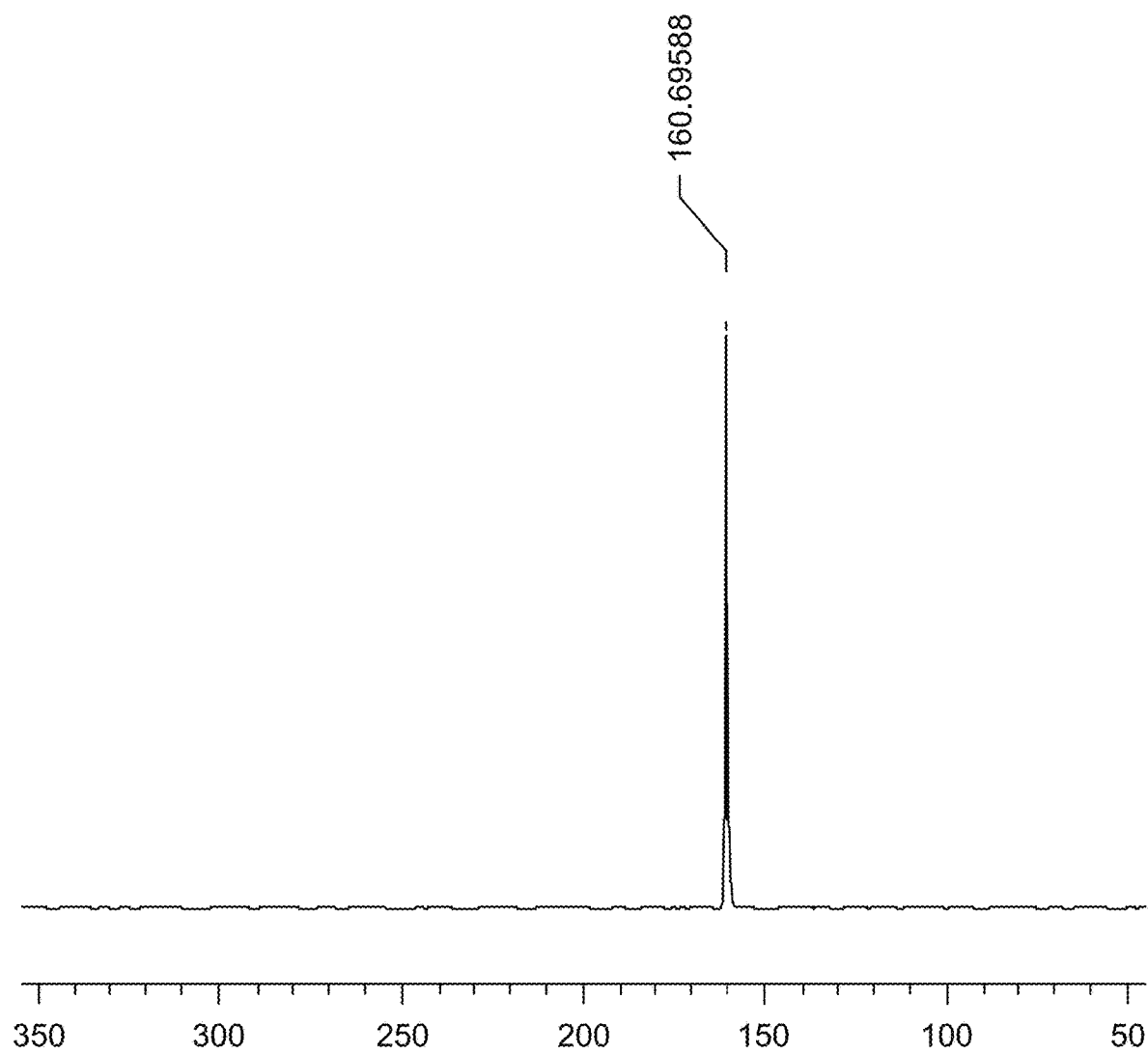
FIG. 14 is a graph illustrating $^{77}$Se NMR spectrum of complex 1 in DMSO-d$_6$.
Figure 15:
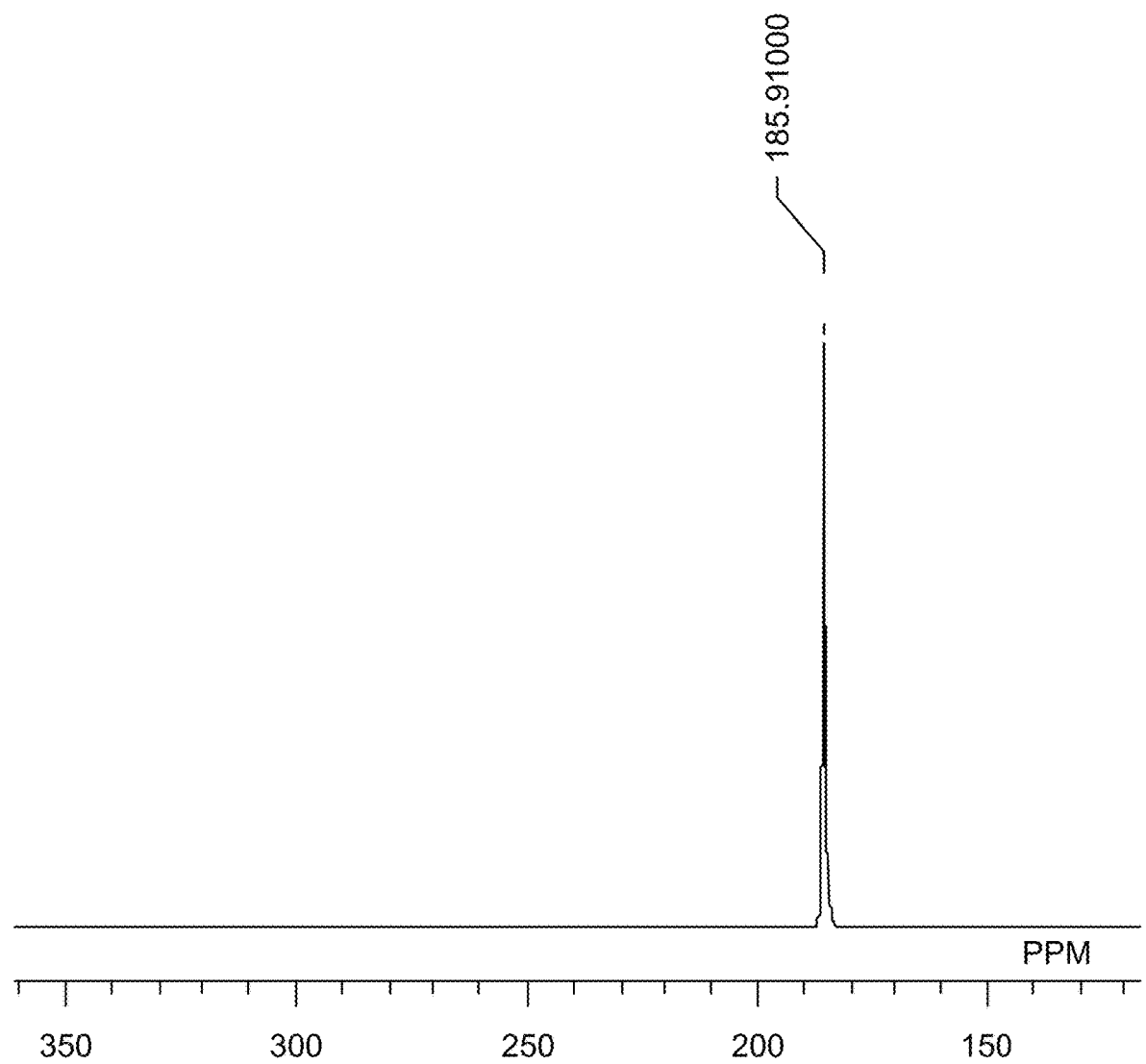
FIG. 15 is a graph illustrating $^{77}$Se NMR spectrum of complex 2 in DMSO-d$_6$.
Figure 16:
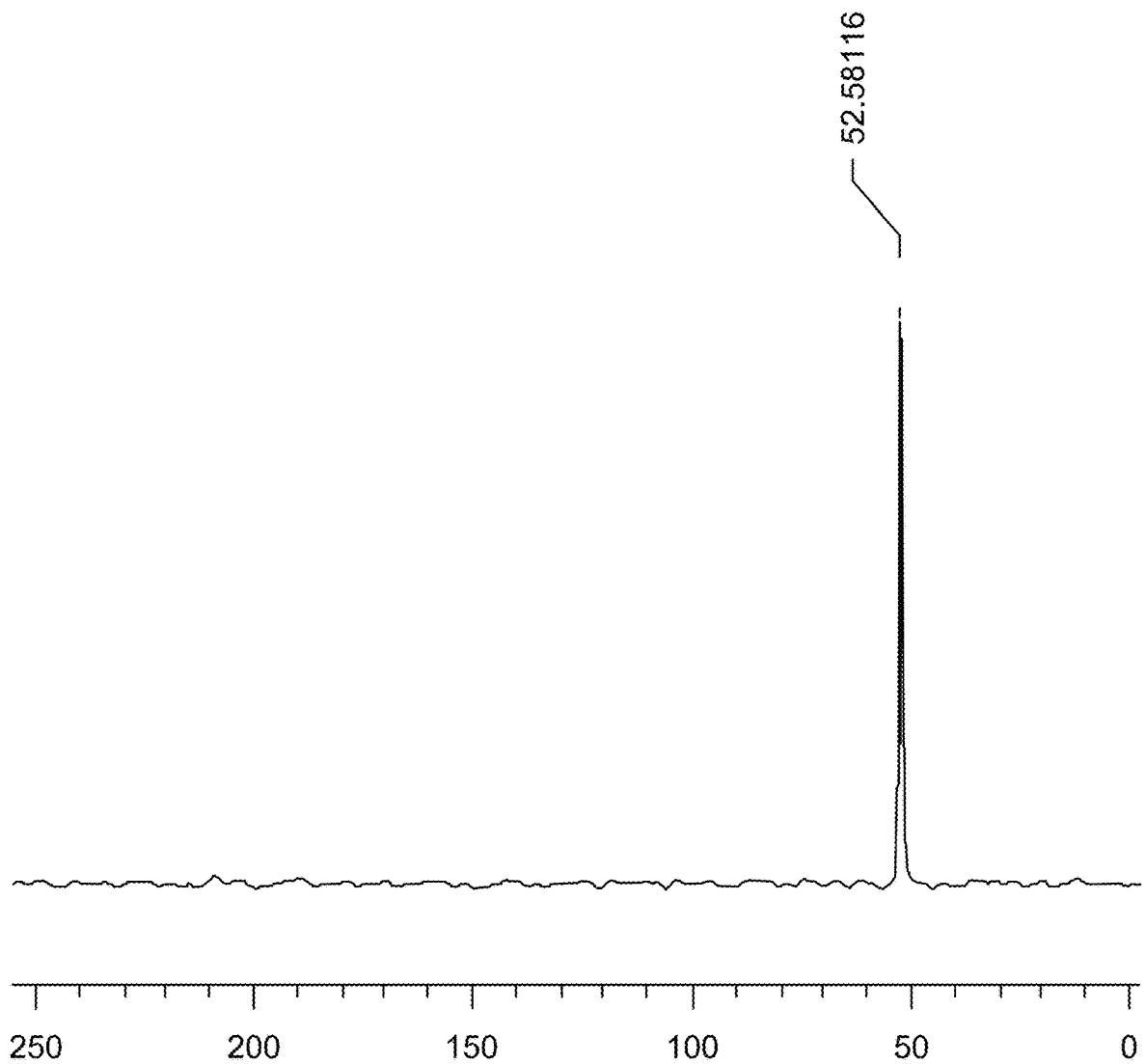
FIG. 16 is a graph illustrating $^{77}$Se NMR spectrum of complex 3 in DMSO-d$_6$.
Figure 17:
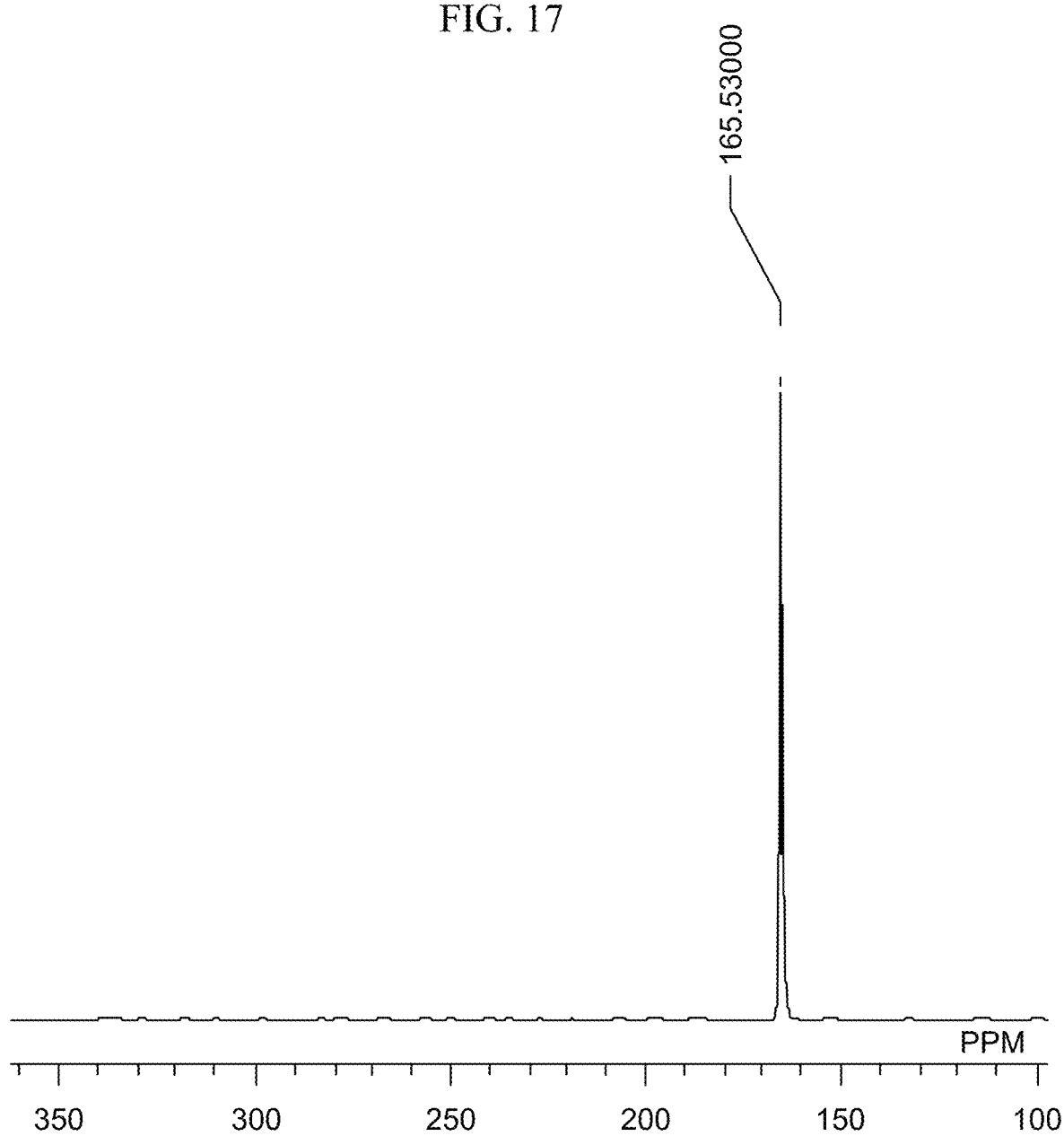
FIG. 17 is a graph illustrating $^{77}$Se NMR spectrum of complex 4 in DMSO-d$_6$.
Figure 18:
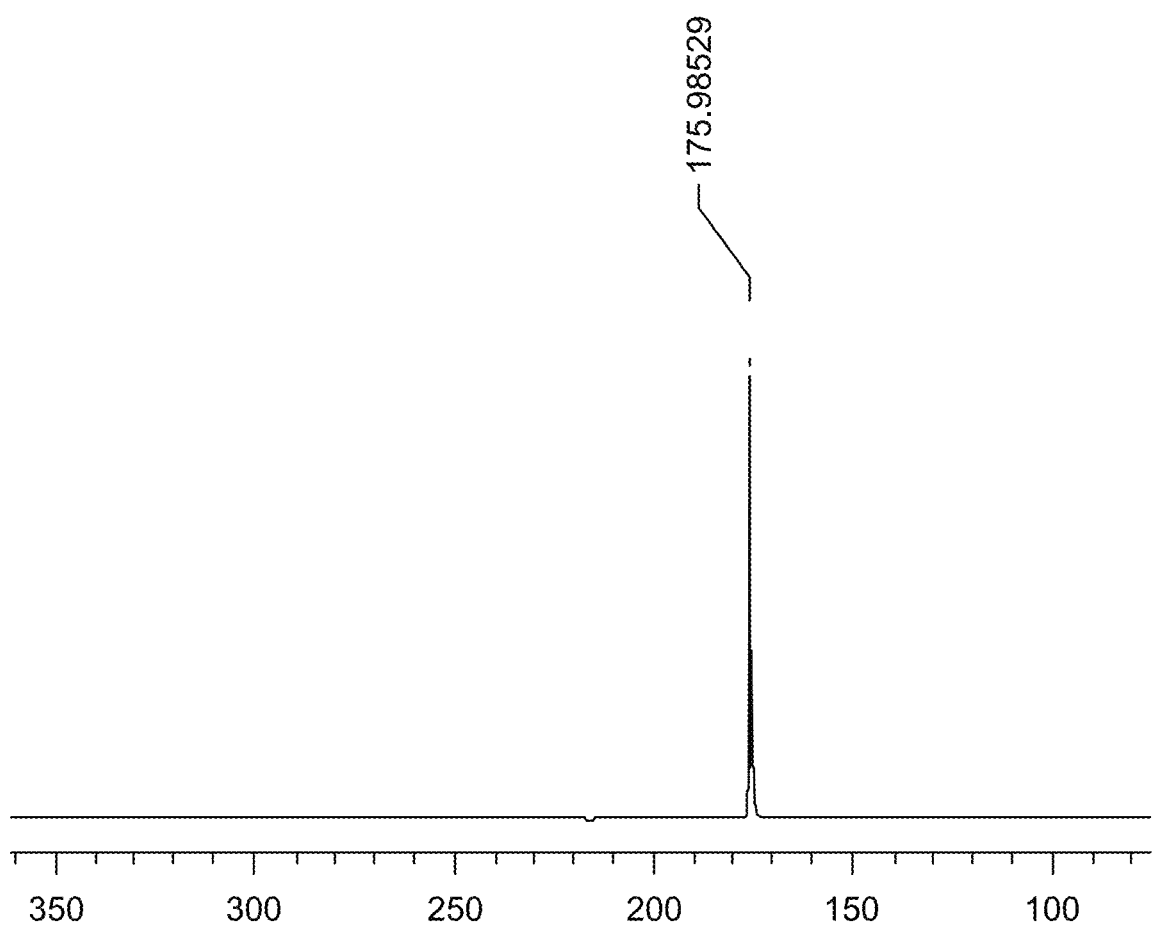
FIG. 18 is a graph illustrating $^{77}$Se NMR spectrum of complex 5 in DMSO-d$_6$.

Docking studies of the synthesized cisplatin derived selenone complexes 1-5 with 1BNA was carried out to understand binding affinity of these ligands with DNA. Results revealed that the complexes were stabilized primarily by both conventional and alkyl hydrogen bonding interactions with the DNA. Table 5 shows the experimental inhibition constant and docking score for top ranked binding conformations. Molecular docking results of DNA shows that all the studied selenone complexes bind strongly with DNA as compared to binding of cisplatin. The binging energy score is more negative for selenone complexes than that of cisplatin. The more negative relative binding energy for complex 5 indicated that among all the complexes, complex 5 binds more strongly to DNA (FIGS. 7A-7C) than any other complex under study. The best possible conformations of the complexes are mainly through the interactions of their two amine groups to the base pairs in the minor groove of DNA, which is stabilized due to stronger hydrogen bonding interactions. Furthermore, the base pairs in the binding site of the target DNA include DT-8, DC-9, DG-10, DC-11, DA-18, DT-19, DT-20, DC-21 and DG-22. All the estimated inhibition constant (K$_i$) for all the docking processes are noticeably and relatively small compared to the one obtained for cisplatin implying that the synthesized complexes bind considerably well to the binding sites and that a relatively low concentration of the complexes is sufficient to maximally occupy a binding site and prompt a physiological response.

TABLE 5

The docking results of cisplatin derived selenone complexes 1-5 with the B-DNA (PDB ID: 1BNA).

| Complex | Estimated Binding Energy (kcal/mol) | Inhibition Constant (μM) |
| --- | --- | --- |
| Cisplatin | −6.74 | 11.45 |
| 1 | −7.68 | 2.35 |
| 2 | −8.73 | 0.40 |
| 3 | −8.85 | 0.33 |
| 4 | −10.29 | 0.079 |
| 5 | −11.35 | 0.0048 |

In summary, the synthesis, spectroscopic characterization, and in vitro cytotoxicity of five new cisplatin derived complexes of selenones (1-5) are reported. The cytotoxic activity of the complexes against A549, HeLa, and HCT-116 human cancer cell lines were evaluated. The complexes 3 and 4 exhibited excellent cytotoxic activity against all cell lines and the complex 1 against HCT-116 cell line. The IC50 data reveals that complexes 3 and 4 are better cytotoxic agents than cisplatin as a commercial drug. Structural changes may substantially alter the DNA binding mode and DNA damage. Docking studies show the binding mode of these compounds with DNA. Binding score for all synthesized compound is higher than that of cisplatin.

The invention claimed is:

1. A platinum(II) complex of formula (Ia),

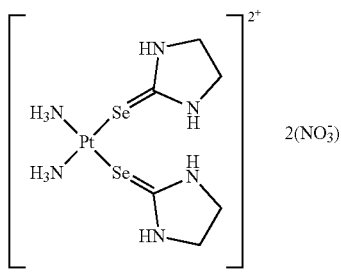

or a pharmaceutically acceptable solvate or tautomer thereof, wherein:

the complex of formula (Ia) is of square planar geometry having a cis-configuration, wherein the 2 NH$_3$ and the 2 selenourea ligands are located in adjacent coordinating positions.

2. A pharmaceutical composition, comprising:
the platinum(II) complex of formula (Ia) of claim 1; and
a pharmaceutically acceptable carrier and/or excipient.

3. The pharmaceutical composition of claim 2, wherein the platinum(II) complex of formula (Ia) is present in the pharmaceutical composition in a concentration of 0.1 to 100 μM, relative to a total volume of the pharmaceutical composition.

4. The pharmaceutical composition of claim 2, wherein the pharmaceutically acceptable carrier and/or excipient comprises dimethyl sulfoxide.

5. A method for treating cancer in a person in need thereof, comprising:
administering to the person in need thereof a therapeutically effective amount of the platinum(II) complex of formula (Ia) of claim 1,
wherein the cancer is at least one selected from the group consisting of cervical cancer, lung cancer, and colon cancer.

6. The method of claim 5, wherein the therapeutically effective amount of the platinum (II) complex of formula (Ia) is from 0.01 to 100 mg/kg of the platinum(II) complex of formula (Ia) per body weight of the person in need thereof.

* * * * *

SEQUENCE LISTING

<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: d(CGCGAATTCGCG)2 dodecamer (PDB ID: 1BNA)
    (Dickerson and Drew 1981)

<400> SEQUENCE: 1
cgcgaattcg cg                                                        12